US007445904B2

(12) United States Patent
Südhof et al.

(10) Patent No.: US 7,445,904 B2
(45) Date of Patent: Nov. 4, 2008

(54) CYSTEINE STRING PROTEIN AND ITS ROLE IN NEURODEGENERATIVE DISEASES

(76) Inventors: Thomas C Südhof, 6138 Turner Way, Dallas, TX (US) 75230; Bernd Stahl, Philosophenweg 15, 72076 Tuebingen (DE); Soenke Tobaben, Von-Bar-Str. 29, 37075 Goettingen (DE)

( * ) Notice: Subject to any disclaimer, the term of this patent is extended or adjusted under 35 U.S.C. 154(b) by 0 days.

(21) Appl. No.: 10/255,989

(22) Filed: Sep. 26, 2002

(65) Prior Publication Data

US 2004/0064844 A1    Apr. 1, 2004

(51) Int. Cl.
  G01N 33/567   (2006.01)
  G01N 33/53    (2006.01)
  A61K 49/00    (2006.01)

(52) U.S. Cl. ............... 435/7.21; 435/7.8; 424/9.1; 424/9.2

(58) Field of Classification Search ............ 800/18; 435/7.2, 7.21, 4; 424/9.1
See application file for complete search history.

(56) References Cited

U.S. PATENT DOCUMENTS

2001/0027182 A1* 10/2001 Zoghbi et al. ............ 514/44

OTHER PUBLICATIONS

Fernandez-Chacon et al (2004). The synaptic vesicle protein CSP-alpha prevents presynaptic degenration. Neuron, 42, 237-251.*
Bowyer and Davies (1999). Changes in mRNA levels for heat shock protein and secretory vesicle associated protein csp 1 after amphetamine exposure.*
Chamberlain and Burgoyne (1999). Cysteine string protein: The chaparone at the synapse.*
Tobaben et al. (2003). Brain-specific isoform of small glutamine rich tetratricopeptide repeat-containing protein binds to hsc70 and cysteine string protein. JBC, 38376-38383.*
Schott, J.m. et al., Annals of neurology, 56, p. 604.*
Tobaben et al., Neuron, vol. 31 pp. 987-999.*
Modrek et al (2002). Nature Genetics. 30, 13-19.*
Bonini (2002). PNAS. 99, 16407-16411.*
Bommel et al (2002). JCB. 159, 563-569.*
Whitton et al (2007). British Journal of pharmacology. 150, 963-976.*
Hardy et al (2006) Ann Neurol. 60, 389-398.*
Smith et al (2001). Neurobiology of Disease. 8, 1017-1026.*
Auluck; P.K. Chan, H.Y., Trojanowski, J.Q., Lee, V.M., and Bonini, N.M. (2002). Chaperone suppression of alpha-synuclein toxicity in a Drosophila model for Parkinson's disease. Science 295(5556):865-868.
Hartl, F.U., and Hayer-Hartl, M. (2002). Molecular chaperones in the cytosol: from nascent chain to folded protein. Science 295:1852-1858.
Schoch, S., Castillo P.E., Jo T., Mukherjee K., Geppert M., Wang Y., Schmitz F., Malenka R.C. and Südhof, T.C. (2002) RIM1α forms a protein scaffold for regulating neurotransmitter release at the active zone. Nature 415:321-326.

Bronk B., Wenniger J.J., Dawson-Scully K., Guo X., Hong S., Atwood H.L. and Zinsmaier K.E. (2001) Drosophila Hsc70-4 is critical for neurotransmitter exocytosis in vivo. Neuron 30:475-488.
Fernandez-Chacon, R., Konigstorfer, A., Gerber, S.H., Garcia, J., Matos, M.F., Stevens, C.F., Brose, N., Rizo, J., Rosenmund, C., Südhof, T.C. (2001) Synaptotagmin I functions as a calcium regulator of release probability. Nature 410:41-9.
Cummings, C.J., Sun, U., Opal, P., Antalffy, B., Mestril, R., Orr, H.T., Dillmann, W.H., and Zoghbi, H.Y. (2001). Over-expression of inducible HSP70 chaperone suppresses neuropathology and improves motor function in SCA1 mice. Hum. Mol. Genet. 10:1511-1518.
Goedert, M. (2001). Alpha-synuclein and neurodegenerative diseases. Nat. Rev. Neurosci. 2:492-501.
Selkoe, D.J. (2001). Alzheimer's disease: genes, proteins, and therapy. Physiol. Rev. 81:741-766.
Sherman, M.Y., and Goldberg, A.L. (2001). Cellular defenses against unfolded proteins: a cell biologist thinks about neurodegenerative diseases. Neuron 29:15-32.
Tobaben, S., Thakur, P., Fernandez-Chacon, R., Südhof, T.C., Rettig, J., Stahl, B. (2001) A trimeric protein complex functions as a synaptic chaperone machine. Neuron 31:987-999.
Dawson-Scully K., Bronk P., Atwood H.L. and Zinsmaier K.E. (2000) Cysteine-string protein increases the calcium sensitivity of neurotransmitter exocytosis in Drosophila J. Neurosci. 20:6039-6047.
Fernandez-Funez, P., Nino-Rosales, M.L., de Gouyon, B., She, W.C., Luchak, J.M., Martinez, P., Turiegano, E. Benito, J., Capovilla, M., Skinner, P.J., McCall, A., Canal, I., Orr, H.T., Zoghbi, H.Y., Botas, J. (2000). Identification of genes that modify ataxin-1-induced neurodegeneration. Nature 408:101-106.
Graham M.E. and Burgoyne R.D. (2000) Comparison of cysteine string protein (Csp) and mutant alpha-SNAP overexpression reveals a role for csp in late steps of membrane fusion in dense-core granule exocytosis in adrenal chromaffin cells. J. Neurosci, 20:1281-1289.
Kazemi-Esfarjani, P., and Benzer, S. (2000). Genetic suppression of polyglutamine toxicity in Drosophila. Science 287:1837-1840.
Lao G., Scheuss V., Gerwin C.M., Su Q., Mochida S., Rettig J. and Sheng Z.H. (2000) Syntaphilin: a syntaxin-1 clamp that controls SNARE assembly. Neuron 25:191-201.

(Continued)

Primary Examiner—David Romeo
Assistant Examiner—Steven H Standley
(74) Attorney, Agent, or Firm—Baker Botts LLP

(57) ABSTRACT

The present invention relates to in vitro and in vivo assays for the identification of agents that are useful in the treatment of neurodegenerative diseases that are associated with defects in protein folding. The present further relates to in vitro and in vivo assays for the identification of agents that contribute to the neurodegenerative processes which occur in these diseases. The present invention also relates to in vitro and in vivo models of neurodegenerative diseases. These assays and models will be useful in further understanding the pathogenesis of various neurodegenerative diseases in which defects in protein folding have been implicated, in identifying additional endogenous or environmental factors that contribute to the etiologies of these diseases, and in developing effective therapies for the prevention and/or treatment of these diseases.

3 Claims, 27 Drawing Sheets

OTHER PUBLICATIONS

Magga J.M., Jarvis S.E., Arnot M.I., Zamponi G.W. and Braun J.E. (2000) Cysteine string protein regulates G protein modulation of N-type calcium channels. *Neuron* 28:195-204.

Schmitz F., Königstorfer A., and Südhof T.C. (2000) RIBEYE, a component of synaptic ribbons: A protein's journey through evolution provides insight into how synaptic ribbons function. *Neuron* 28:857-872.

Südhof T.C. (2000) The synaptic vesicle cycle revisited. *Neuron* 28:317-320.

Zoghbi, H.Y., and Orr. H.T. (2000). Glutamine repeats and neurodegeneration. *Annu. Rev. Neurosci.* 23:217-247.

Augustin I., Betz A., Herrmann C., Jo T. and Brose N. (1999) Differential expression of two novel Munc13 proteins in rat brain. *Biochem. J.* 337:363-371.

Blatch G.L. and Lässle M. (1999) The tetratricopeptide repeat: a structural motif mediating protein—protein interactions. *Bioessays* 21:932-939.

Fink A.L. (1999) Chaperone-mediated protein folding. *Physiol. Rev.* 79:425-449.

Liu F.H., Wu S.J., Hu S.M., Hsiao C.D. and Wang C. (1999) Specific interaction of the 70-kDa heat shock cognate protein with the tetratricopeptide repeats. *J. Biol. Chem.* 274:34425-34432.

Nie Z., Ranjan R., Wenniger J.J., Hong S.N., Bronk P. and Zinsmaier K.E. (1999) Overexpression of cysteine-string proteins in *drosophila* reveals interactions with syntaxin. *J. Neurosci.* 19:10270-10279.

Scales S.J. and Scheller R.H. (1999) Lipid membranes shape up. *Nature* 401:123-124.

Stahl B., Tobaben S. and Südhof T.C. (1999) Two distinct domains in hsc70 are essential for the interaction with the synaptic vesicle cysteine string protein. *Eur. J. Cell Biol.* 78:375-381.

Warrick, J.M., Chan, H.Y., Gray-Board, G.L., Chai, U., Paulson, H.L. and Bonini, N.M. (1999). Suppression of polyglutamine-mediated neurodegeneration in Drosophila by the molecular chaperone HSP70. *Nat. Genet.* 23:425-428.

Wu M.N., Fergestad T., Lloyd T.E., He Y., Broadie K. and Bellen H.J. (1999) Sytaxin 1A interacts with multiple exocytic proteins to regulate neurotrasmitter release in vivo. *Neuron* 23:593-605.

Callahan M.A., Handley M.A., Lee Y.H., Talbot K.J., Harper J.W. and Panganiban A.T. (1998) Functional interaction of human immunodeficiency virus type 1 Vpu and Gag with a novel member of the tetratricopeptide repeat protein family. *J. Virol.* 72:5189-5197.

Chamberlain L.H. and Burgoyne R.D. (1998) The cysteine-string domain of the secretory vesicle cysteine-string protein is required for membrane targeting. *Biochem. J*, 335:205-209.

Cziepluch C., Kordes E., Poirey R., Grewenig A., Rommelaere J. and Jauniaux J.C. (1998) Identification of a novel cellular TRP-containing protein, SGT, that interacts with the nonstructural protein NS1 of parvovirus H-1. *J. Virol.* 72:4149-4156.

Leveque C., Pupier S., Marqueze B., Geslin L., Kataoka M., Takahashi M., De W.M. and Seagar M. (1998) Interaction of cysteine string proteins with the alpha1A subunit of the P/Q-type calcium channel. *J. Biol. Chem.* 273:13488-13492.

Ranjan R., Bronk P. and Zinsmaier K.E. (1998) Cysteine string protein is required for calcium secretion coupling of evoked neurotransmission in drosophila but not for vesicle recycling. *J. Neurosci.* 18:956-964.

von Kriegstein K., Schmitz F., Link E. and Südhof T.C. (1998) Distribution of synaptic vesicle proteins in the mammalian retina identifies obligatory and facultative components of ribbon synapses. *Eur. J. Neurosci.* 11:1335-1348.

Young J.C., Obermann W.M. and Hartl F.U. (1998) Specific binding of tetratricopeptide repeat proteins to the C-terminal 12-kDa domain of hsp90. *J. Biol. Chem.* 273:18007-18010.

Buchner E. and Gundersen C.B. (1997) The DnaJ-like cysteine string protein and exocytotic neurotransmitter release. *Trends Neurosci.* 20:223-227.

Chamberlain L.H. and Burgoyne R.D. (1997) Activation of the ATPase activity of heat-shock proteins Hsc70/Hsp70 by cysteine-string protein. *Biochem. J.* 322:853-858.

Cziepluch, C., Kordes, E., Poirey, R., Grewenig, A., Rommelaere, J. and Jauniaux, J.C. (1997) *Rattus norvegicus* mRNA for small glutamine-rich tetratricopeptide repeat (TPR) containing protein (SGT). GenBank Accession No. AJ222724.

Noji H., Yasuda R., Yoshida M. and Kinosita K. Jr. (1997) Direct observation of the rotation of F1-ATPase. *Nature* 386:299-302.

Braun J.E.A., Wilbanks S.M. and Scheller R.H. (1996) The cysteine string secretory vesicle protein activates Hsc70 ATPase. *J. Biol. Chem.* 271:25989-25993.

Chamberlain L.H., Henry J. and Burgoyne R.D. (1996) Cysteine string proteins are associated with chromaffin granules. *J. Biol. Chem.* 271:19514-19517.

Rosenmund C. and Stevens C.F. (1996) Definiton of the readily releasable pool of vesicles at hippocampal synapses. *Neuron* 16:1197-1207.

Stahl B., Chou J.H., Li C., Südhof T.C. and Jahn R. (1996) Rab3 reversibly recruits rabphilin to synaptic vesicles by a mechanism analogous to raf recruitment by ras. *EMBO J.* 15:1799-1809.

Braun J.E. and Scheller R.H. (1995) Cysteine string protein, a DnaJ family member, is present on diverse secretory vesicles. *Neuropharmacology* 34:1361-1369.

Braun J.E. and Scheller R.H. (1995) Cysteine string protein = 34 kDa DnaJ-hsp40 heat shock-chaperone protein [rats, brain, mRNA Partial, 645 nt]. GenBank Accession No. S81917.

Hendrick J.P. and Hartl F.U. (1995) The role of molecular chaperones in protein folding. *Faseb J*, 9:1559-1569.

Hohfeld J., Minami Y. and Hartl F.U. (1995) Hip, a novel cochaperone involved in the eukaryotic Hsc70/Hsp40 reaction cycle. *Cell* 83:589-598.

Mennerick S. and Zorumski C.F. (1995) Paired-pulse modulation of fast excitatory synaptic currents in microcultures of rat hippocampal neurons. *J. Physiol*, 488:85-101.

Südhof T.C. (1995) The synaptic vesicle cycle: a cascade of protein-protein interactions. *Nature*, 375:645-653.

Ungewickell E., Ungewickell H., Holstein S.E., Lindner R., Prasad K., Barouch W., Martin B., Greene L.E. and Eisenberg E. (1995) Role of auxilin in uncoating clathrin-coated vesicles. *Nature* 378:632-635.

Walch-Solimena C., Blasi J., Edelmann L., Chapman E.R., von Mollard G. and Jahn R. (1995) The t-SNAREs syntaxin 1 amd SNAP-25 are present on organelles that participate in synaptic vesicle recycling. *J. Cell Biol.* 128:637-645.

Geppert, M., Ullrich, B., Green, D.G., Takei, K., Daniels, L., De Camilli, P., Sudhof, T.C., Hammer, R.E. (1994) Synaptic targeting domains of synapsin I revealed by transgenic expression in photoreceptor cells. *EMBO J* 13:3720-3727.

Gundersen C.B., Mastrogiacomo A., Faull K. and Umbach J.A. (1994) Extensive lipidation of a Torpedo cysteine string protein. *J. Biol. Chem.* 269:19197-19199.

Mastrogiacomo A., Parsons S.M., Zampighi G.A., Jenden D.J., Umbach J.A. and Gundersen C.B. (1994) Cysteine string proteins: a potential link between synaptic vesicles and presynaptic $Ca^{2+}$ channels. *Science* 263:981-982.

Szabo A., Langer T., Schroder H., Flanagan J., Bukau B. and Hartl F.U. (1994) The ATP hydrolysis-dependent reaction cycle of the *Escherichia coli*Hsp70 system DnaK, DnaJ, and GrpE. *Proc. Natl. Acad. Sci. USA* 91:10345-10349.

Zinsmaier K.E., Eberle K.K., Buchner E., Walter N. and Benzer S. (1994) Paralysis and early death in cysteine string protein mutants of Drosophila. *Science* 263:977-980.

Rosahl T.W., Geppert M., Spillane D., Herz J., Hammer R.E., Malenka R.C. and Südhof T.C. (1993) Short-term synaptic plasticity is altered in mice lacking synapsin I. *Cell* 75:661-670.

Vojtek A.B., Hollenberg S.M. and Cooper J.A. (1993) Mammalian Ras interacts directly with the serine/threonine kinase Raf. *Cell* 74:205-214.

Gundersen C.B. and Umbach J.A. (19920 Suppression cloning of the cDNA for a candidate subunit of a presynaptic calcium channel. *Neuron* 9:527-537.

Rothermel, E., Detzler, E., Walter, L., Levan, G. and Gunther, E. *R. norvegicus* Hsc70-ps1 gene. GenBank Accession No. X70065, Aug. 1, 1996.

Bekkers J.M. and Stevens C.F. (1991) Excitatory and inhibitory autaptic currents in isolated hippocampal neurons maintained in culture. *Proc. Natl. Acad. Sci. USA* 88:7834-7838.

Guan K.L. and Dixon J.E. (1991) Eukaryotic proteins expressed in *Escherichia coli*: an improved thrombin cleavage and purification procedure of fusion proteins with glutathione S-transferase. *Anal. Biochem.* 192:262-267.

Sasaki T., Kikuchi A., Araki S., Hata Y., Isomura M., Kuroda S. and Takai Y. (1990) Purification and characterization from brain cytosol of a protein that inhibits the dissociation of GDP from, and the subsequent binding of GTP to smg p25A, a ras p21-like GTP-binding protein. *J. Biol. Chem*, 265:2333-2337.

Zinsmaier K.E., Hofbauer A., Heimbeck G., Pflugfelder G.O., Buchner S. and Buchner E. (1990) A cysteine-string protein is expressed in retina and brain of Drosophila. *J. Neurogenet.* 7:15-29.

Schiestl R.H. and Gietz R.D. (1989) High efficiency transformation of intact yeast cells using single stranded nucleic acids as a carrier. *Curr. Genet*, 16:339-346.

Smith D.B. and Johnson K.S. (1988) Single-step purification of polypeptides expressed in *Escherichia coli* as fusions with glutathione S-transferase. *Gene* 67:31-40.

Jahn R., Schiebler W., Ouimet C. and Greengard P. (1985) A 38,000-dalton membrane protein (p38) present in synaptic vesicles. *Proc. Natl. Acad. Sci. USA* 82:4137-4141.

Laemmli U.K. (1970) Cleavage of structural proteins during the assembly of the head of bacteriophage T4. *Nature* 227:680-685.

Towbin H., Staehelin T. and Gordon J. (1979) Electrophoretic transfer of proteins from polyacrylamide gels to nitrocellulose sheets: procedure and some applications. *Proc. Natl. Acad. Sci. USA* 76:4350-4354.

\* cited by examiner

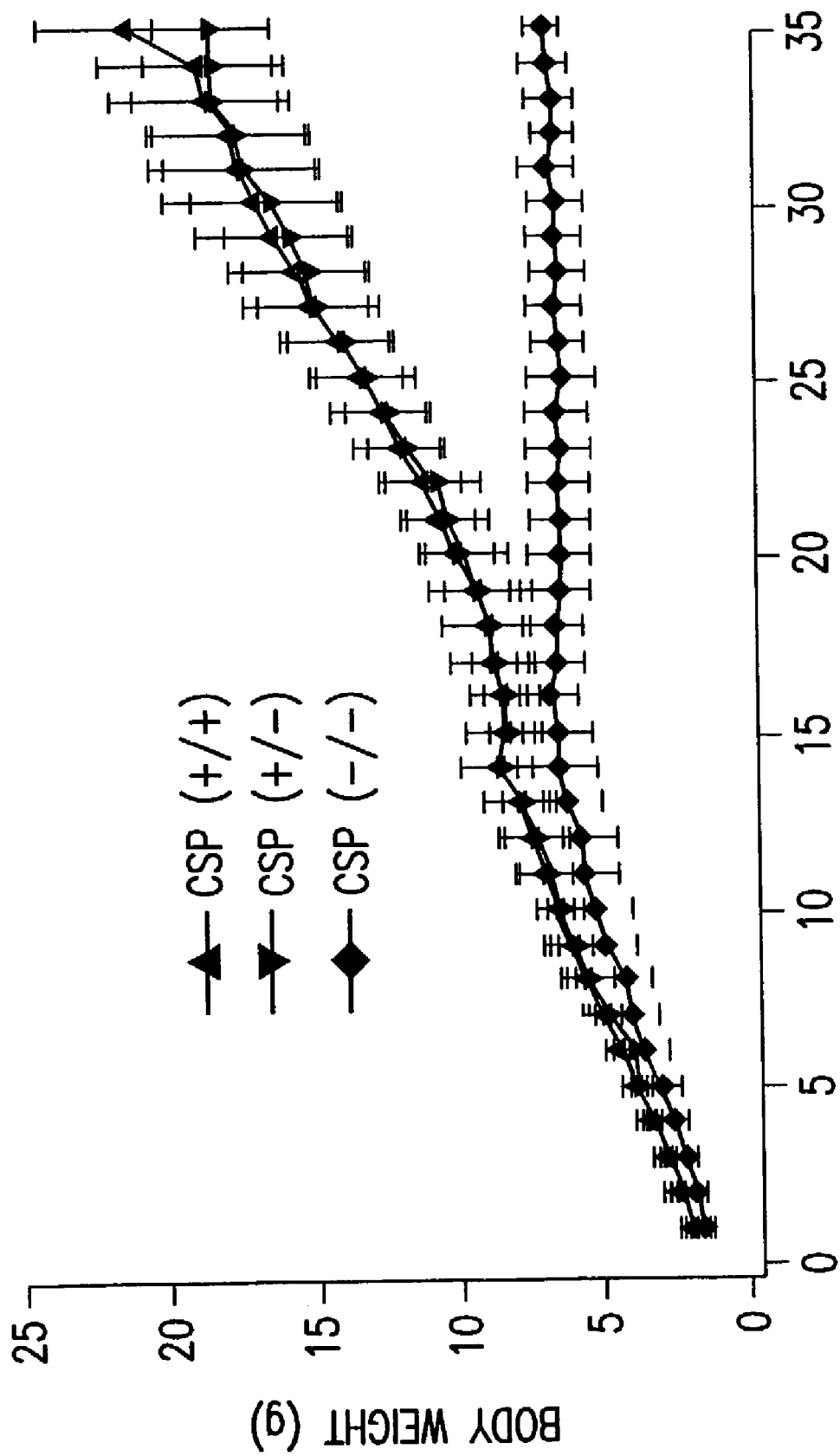

Wild Type

Anti-CSP

CSP KO

Anti-CSP

CSP KO

Anti-Synaptoporin

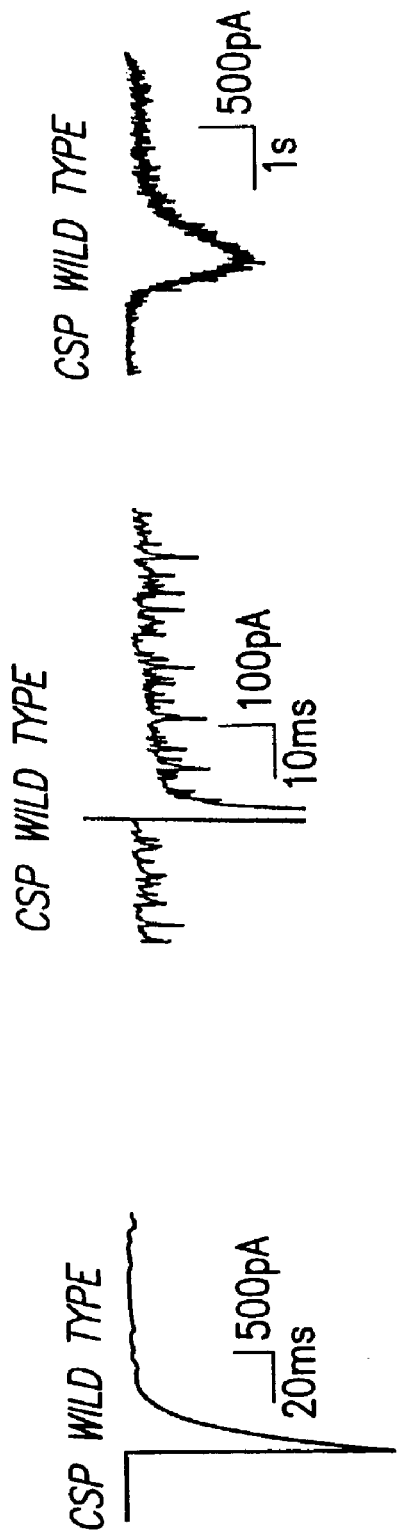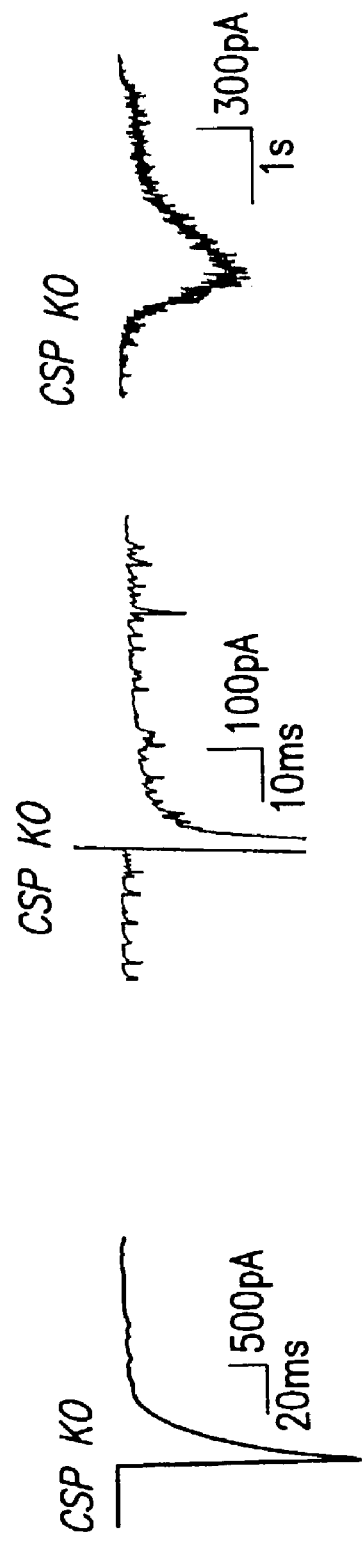

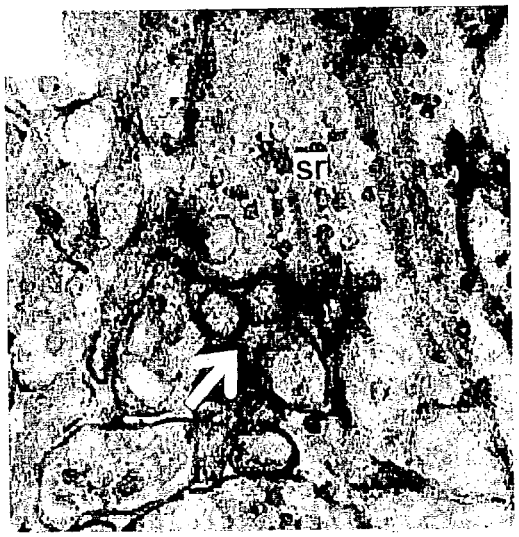 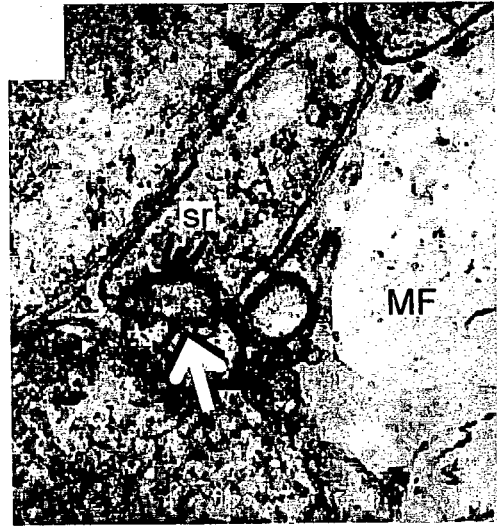
FIG.9A  FIG.9B
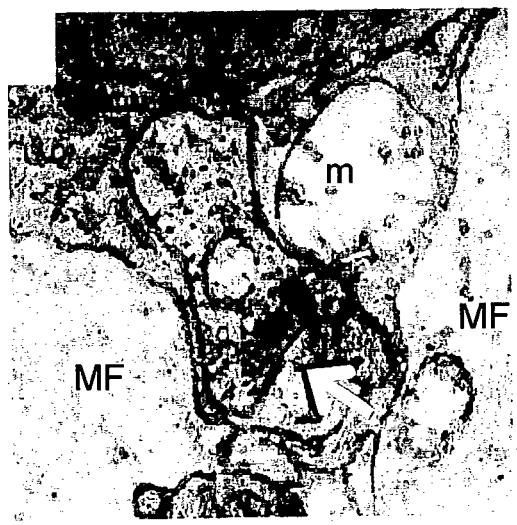 
FIG.9C  FIG.9D

US 7,445,904 B2

CYSTEINE STRING PROTEIN AND ITS ROLE IN NEURODEGENERATIVE DISEASES

SPECIFICATION

The subject matter described herein was supported, at least in part, by funds provided by the United States Government. Accordingly, the United States Government may have certain rights to this invention.

INTRODUCTION

The present invention relates to in vitro and in vivo assays for the identification of agents that can be useful in the treatment of neurodegenerative diseases that are associated with defects in protein folding. The present invention further relates to in vitro and in vivo assays for the identification of agents that could contribute to the neurodegenerative processes which occur in these diseases. The present invention also relates to in vitro and in vivo models of neurodegenerative diseases. These inventions are based, at least in part, on the observations that 1) cysteine string protein (CSP) forms a complex in the presynaptic nerve terminal with the heat shock protein Hsc70 and the small glutamine-rich tetratricopeptide (TPR) protein (SGT), 2) that this complex constitutes an ATP-dependent presynaptic chaperone machine that is essential in maintaining long-term synaptic function, and 3) that mice in which the CSP gene has been disrupted by insertional mutagenesis (CSP knockout mice) suffer from neuronal degeneration that becomes apparent in synapses formed by motoneurons and retinal neurons among other neuronal cell populations. Degeneration of motoneuron synapses in turn leads to ascending motor disease. These assays and models are useful in understanding the pathogenesis of various neurodegenerative diseases in which defects in protein folding have been implicated, in identifying additional endogenous or environmental factors that could contribute to the etiologies of these diseases, and in developing effective therapies for the prevention and/or treatment of these diseases.

BACKGROUND OF INVENTION

1. The Role of Cysteine String Protein in Synaptic Function

The exocytotic release of neurotransmitter from nerve terminals is a fundamental process underlying most intercellular communication in the nervous system. Synaptic vesicles, the central players in this process, undergo a complex cycle of fusion and fission events. They fuse with the presynaptic membrane in response to a rise in the intracellular $Ca^{2+}$ concentration, and release their neurotransmitter cargo into the synaptic cleft. The vesicle membrane is then retrieved by endocytosis (Südhof, 1995, Nature 375:645-653; Scales and Scheller, 1999, Nature 401:123-124; Südhof, 2000, Neuron 28:317-320 2000).

In the last ten years, enormous progress has been made in identifying and characterizing the essential protein machinery involved in organizing and maintaining the synaptic vesicle cycle. One component of this complex protein machinery is the cysteine string protein (CSP), which is thought to have an important function in the exocytotic release of neurotransmitter, hormones, and enzyme precursors (Buchner and Gundersen, 1997, Trends Neurosci. 20:223-227). CSP is localized on synaptic vesicles (Mastrogiacomo et al., 1994, Science 263:981-982), chromaffin granules (Chamberlain et al., 1996, J. Biol. Chem. 271:19514-19517), and zymogen granules (Braun and Scheller, 1995, Neuropharmacology 34:1361-1369). It is highly conserved during evolution (Buchner and Gundersen, 1997, Trends Neurosci. 20:223-227), reflected by an overall amino acid identity of almost 55% between rat and Drosophila CSP. Due to a unique structural feature, a string of 11 cysteines flanked on either side by two additional cysteines, it was named cysteine string protein (Zinsmaier et al., 1990, J Neurogenet. 7:15-29). Most of the cysteine residues are palmitoylated and required for membrane targeting of CSP (Gundersen et al., 1994, J. Biol. Chem. 269:19197-19199; Chamberlain and Burgoyne, 1998, Biochem. J. 335:205-209). Another striking feature of CSP is that it contains a J domain at the N terminus. The J domain comprises a stretch of 70 amino acids evolutionarily conserved from E. coli to man (Fink, 1999, Physiol. Rev. 79:425-449).

The biological function of CSP has remained elusive. In Drosophila, deletion of CSP is lethal for a great majority of flies (Zinsmaier et al., 1994, Science 263:977-980). However, a small percentage of CSP null mutants survived and could be analyzed with electrophysiological methods. CSP "knockout" flies showed an impaired presynaptic neuromuscular transmission accompanied with a dramatic loss of synaptic vesicles. It has been suggested that CSP might function in regulating presynaptic $Ca^{2+}$ channels based on the finding that injection of CSP antisense RNA into Xenopus oocytes inhibited the activity of omega-conotoxin sensitive $Ca^{2+}$ channels (Gundersen and Umbach, 1992, Neuron 9:527-537). Indeed, a direct interaction of CSP with the α1A subunit of P/Q-type $Ca^{2+}$ channels and an indirect interaction via G protein modulation was reported (Leveque et al., 1998, J. Biol. Chem. 273:13488-13492; Magga et al., 2000, Neuron 28:195-204). Drosophila CSP null mutants showed a wild-type like release of neurotransmitter when a $Ca^{2+}$ ionophore was used to trigger exocytosis, implying that CSP functions in the coupling of the $Ca^{2+}$ signal to secretion (Ranjan et al., 1998, J. Neurosci. 18:956-964). Consistent with this hypothesis, the temperature-sensitive inhibition of neuromuscular transmission in CSP null mutants is correlated with a rise in the intracellular $Ca^{2+}$ concentration, suggesting that CSP increases the $Ca^{2+}$ sensitivity of the exocytotic machinery (Dawson-Scully et al, 2000, J. Neurosci. 20:6039-6047). In Drosophila, an interaction between CSP and the t-SNARE syntaxin-1A has been reported (Nie et al., 1999, J. Neurosci. 19:10270-10279; Wu et al., 1999, Neuron 23:593-605) whereas in vertebrates, CSP was found to bind to synaptobrevin/VAMP but not to syntaxin (Leveque et al, 1998, J. Biol. Chem. 273:13488-13492).

Compelling evidence has been presented that CSP interacts with members of the heat-shock family Hsp70 (Braun et al., 1996, Neuropharmacology 34:1361-1369; Chamberlain and Burgoyne, 1997, Biochem. J. 322:853-858; Stahl et al., 1999, Eur. J. Cell Biol. 78:375-381). This interaction was originally found by means of an ATPase assay (Braun et al., 1996, Neuropharmacology 34:1361-1369). CSP strongly activated the Hsc70 ATPase. Thereafter, a direct binding of Hsc70 to the J domain of CSP could be shown (Stahl et al., 1999, Eur. J. Cell Biol. 78:375-381). Among other functions, members of the Hsp70 family, like Hsc70, act as molecular chaperones (Hendrick and Hartl, 1995, Faseb J. 9:1559-1569).

Molecular chaperone complexes act to catalyze the proper folding of newly synthesized proteins and renature proteins that have become denatured in response to various forms of cellular stress or injury (Hartl and Hayer-Hartl, 2002). Chaperones are also required for the translocation of proteins across cell membranes, play a role in macromolecular assembly and disassembly, mediate the degradation of proteins in the proteasome, and participate in various signal transduction pathways that induce gene transcription in response to stress, including those that act to suppress apoptosis.

Using the yeast two-hybrid system, a novel CSP binding partner, termed SGT, also has been identified. SGT was originally discovered because of its putative interaction with envelope proteins of two viruses, i.e. human immunodeficiency virus type 1 and parvovirus H-1 (Callahan et al., 1998, *J. Virol.* 72:5189-5197; Czieplich et al., 1998, *J. Virol.* 72:4149-4156). A detailed sequence analysis revealed that SGT contains three tandem tetratricopeptide repeat domains (TPRs). The TPR domain is a degenerate 34 amino acid sequence found in a wide variety of proteins, present in tandem arrays of 3 to 16 motifs, which form scaffolds to mediate protein-protein interactions. Currently, more than 50 proteins are known to contain TPR motifs, present in organisms as diverse as bacteria and humans (Blatch and Lässle, 1999, *Bioessays* 21:932-939).

2. Role of Protein Folding in Neurodegenerative Diseases

Neurodegenerative disorders are increasingly common in Western societies. For example, in the United States alone, more than 6 million people are afflicted with Alzheimer's disease (AD) and Parkinson's disease (PD). AD is the most common senile dementia, affecting an approximately 10% of people over the age of 65, whereas PD is the most common movement disorder, affecting 1%-2% of this same population group. Other neurodegenerative diseases whose incidences have been rising include Huntington's disease (HD) and spinocerebellar ataxias (SCAs).

Although the genetic basis of most neurodegenerative diseases appears to be highly heterogeneous, many of these disorders display a common pattern of deposition of misfolded, aggregated, and ubiquitinated proteins followed by cell loss. For example, in AD, neurofibrillary tangles comprised of the Tau protein are found intracellularly and plaques comprised of $\beta$-amyloid (A$\beta$) peptides are found extracellularly in the neocortex and hippocampus where cell loss is most prominent (Selkoe, 2001, *Physiol. Rev.* 81:741-766). In PD, intracellular lesions known as Lewy bodies, comprised mainly of $\alpha$-synuclein, are found in the cytoplasm of dopaminergic neurons of the substantia nigra, where cell loss subsequently occurs (Goedert, 2001, *Nat. Rev. Neurosci.* 2:492-501). In HD, the protein deposits are comprised of huntingtin, are form intranuclear and cytoplasmic inclusion bodies in neurons of the striatum and cerebral cortex (Zoghbi and Orr, 2000, *Annu. Rev. Neurosci.* 23:217-247). The presence of these aggregates suggests a defect in the ability of the cellular machinery that normally acts to prevent the formation or accumulation of misfolded proteins, namely protein chaperone complexes.

3. Current Treatments for Neurodegenerative Diseases and Their Limitations

Although the various neurodegenerative diseases are etiologically distinct, treatment strategies can be generally divided into two classes—palliative and "disease-altering." Palliative strategies are those designed to alleviate symptoms and include, for example, the use of dopamine agonists or L-dopa in the treatment of PD to compensate for the deficits in dopamine neurotransmission caused by the loss of dopaminergic neurons from the substantia nigra, or the use of acetylcholinesterase inhibitors or cholinergic agonists in the treatment of AD to counteract the loss of cholinergic neurons from the neocortex and hippocampus. While somewhat beneficial in patient management, these approaches fail to alter the underlying pathophysiological process that lead to the diseases being treated A variety of truly "disease-altering" approaches have been proposed or are being examined in preclinical and clinical studies of various neurodegenerative diseases. For example, pharmacological approaches designed to prevent the formation of the protein aggregates (e.g. $\beta$- or $\gamma$-secretase inhibitors to block the proteolytic processing of APP in AD), are being designed and tested. However, as many of the enzymes that lead to the formation of protein deposits are not involved in the processing of a wide variety of proteins, most of which are not involved in the disease process, the specificity and toxicity of these compounds is suspect.

Various immunological approaches are also being examined as a means of reducing the burden of protein plaques in the brain. For example, vaccination of AD patients with A$\beta$42 has been proposed as a means of clearing amyloid plaque from the brains of patients with AD. Unfortunately, at least some patients receiving this treatment in phase IIA clinical trials experienced significant and potentially life-threatening brain inflammation.

A great amount of attention has also been directed toward various restorative approaches to the treatment of neurodegenerative diseases, including transplantation or cell- or gene-based therapies. Though conceptually interesting, these approaches have many practical limitations. For transplantation, these include the lack of donor material for implantation, the failure of the transplanted material to engraft into the recipient and forge new synaptic connections, and the complexity and expense associated with brain surgery. In addition to these problems, cell-based therapies are further hindered by our paucity of knowledge concerning the identity of neuronal stem cells while gene-based therapies are beset by problems associated with gene delivery and gene regulation.

Although several of the "disease-altering" approaches detailed above show some promise, none are completely without inherent limitations. Thus, there is a strong need for the development of additional therapeutic modalities for the treatment of neurodegenerative diseases.

4. Utility of Molecular Chaperones in the Treatment of Neurodegenerative Diseases Many publications have now demonstrated that overexpression of the Hsp70 and Hsp40 families of chaperones can suppress the aggregation and toxicity of polyglutamine-containing proteins such a huntingtin (Sherman and Goldberg, 2001). Perhaps the most compelling data in support of a role for chaperones in neurodegenerative diseases associated with protein misfolding comes from in vivo studies performed in fruit fly and mouse models of neurodegenerative disorders (Warrick et al., 1999; Fernandez-Funez et al., 2000; Kazemi-Esfarjani and Benzer, 2000; Cummings et al., 2001; Auluck et al., 2002). For example, overexpression of human Hsp70 completely suppressed the external eye defects mediated by the eye-specific expression of an expanded polyglutamine-containing protein in a *Drosophila* model of Machado-Joseph disease (Warrick et al., 1999). Overexpression of Hsp70 in a mouse model of spinocerebellar ataxia (SCA1) also reduced the neurodegeneration present in these animals, as well as ameliorating the behavioral phenotype of the treated animals (Cummings et al., 2001). Interestingly, in both studies, there appeared to be little or no change in the formation of polyglutamine-containing protein aggregates as determined by light microscopy (Warrick et al., 1999; Cummings et al., 2001). Similar results have been observed in *Drosophila* models of PD (Auluck et al., 2002). These findings suggest that chaperones act by changing the nature of the aggregates in such a way as to reduce their toxicity rather than completely preventing their formation. Alternatively, the beneficial effects of chaperone overexpression observed in these studies may stem from the other roles that chaperones play within the cell, such as protein trafficking or signal transduction. In either event, these results clearly show the value of chaperones as useful targets for pharmacological intervention in neurodegenerative diseases.

In accordance with the present invention, it has been discovered 1) cysteine string protein (CSP) forms a complex in the presynaptic nerve terminal with the heat shock protein Hsc70 and the small glutamine-rich tetratricopeptide (TPR) protein (SGT), 2) that this complex constitutes an ATP-dependent presynaptic chaperone machine that is essential in maintaining long-term synaptic function, and 3) that mice in which the CSP gene has been disrupted by insertional mutagenesis (CSP knockout mice) suffer from neuronal degeneration. These discoveries have permitted the development of assays and models that are useful in understanding the pathogenesis of various neurodegenerative diseases in which defects in protein folding have been implicated, in identifying additional endogenous or environmental factors that could contribute to the etiologies of these diseases, and in developing effective therapies for the prevention and/or treatment of these diseases.

SUMMARY OF THE INVENTION

The present invention relates to in vitro and in vivo assays for the identification of agents that are useful in the treatment of neurodegenerative diseases that are associated with defects in protein folding. The present invention further relates to in vitro and in vivo assays for the identification of agents that contribute to the neurodegenerative processes which occur in these diseases. The present invention also relates to in vitro and in vivo models of neurodegenerative diseases. These inventions are based, at least in part, on the observations that 1) cysteine string protein (CSP) forms a complex in the presynaptic nerve terminal with the heat shock protein Hsc70 and the small glutamine-rich tetratricopeptide (TPR) protein (SGT), 2) that this complex constitutes a presynaptic ATP-dependent chaperone machine that is essential in maintaining long-tern synaptic function, and 3) that mice in which the CSP gene has been disrupted by insertional mutagenesis (CSP knockout mice) exhibit degeneration of lower spinal motor neurons among other neuronal cell populations, leading to ascending motor disease. These assays and models will prove useful in further understanding the pathogenesis of various neurodegenerative diseases in which defects in protein folding have been implicated, in identifying additional endogenous or environmental factors that contribute to the etiologies of these diseases, and in developing effective therapies for the prevention and/or treatment of these diseases.

DEFINITIONS

The following abbreviations are used throughout this application: ADP—adenosine diphosphate; ATP—adenosine triphosphate; CSP—Cysteine String Protein; Hsc70—70 kDa heat-shock cognate protein; NSF—N-ethylmaleimide-sensitive factor; SGT—small glutamine-rich TPR protein; SNAP—soluble NSF attachment protein; SNARE—soluble NSF attachment protein receptor; TPR—tetratricopeptide repeat.

DESCRIPTION OF THE DRAWINGS

FIGS. 4A-C shows the overt phenotypic manifestations of the CSP KO mice. A. Photograph of wild-type and homozygous CSP KO mice. B. Increase in body weight of homozygous wild-type, heterozygous CSP KO and homozygous CSP KO mice at various time points after birth (in days). C. Survival of homozygous wild-type, heterozygous CSP KO and homozygous CSP KO mice at various time points after birth (in days).

FIGS. 6A-I shows the results of electrophysiological studies of synaptic charge (FIG. 6A, D, and G), vesicular pool size (FIG. 6B, E, and H) and vesicular release probability (FIG. 6C, F, and I) in homozygous wild-type (A-C) and homozygous CSP KO (D-F) mice. Data shown are means +/− SEMs.

FIGS. 9A-D shows low-power electron micrographs of ribbon synapses from the retinae of CSP knockout mice (A-D).). Again, degeneration of the synaptic terminals in the CSP KO mice is evident.

DETAILED DESCRIPTION OF THE INVENTION

Figure 1A:
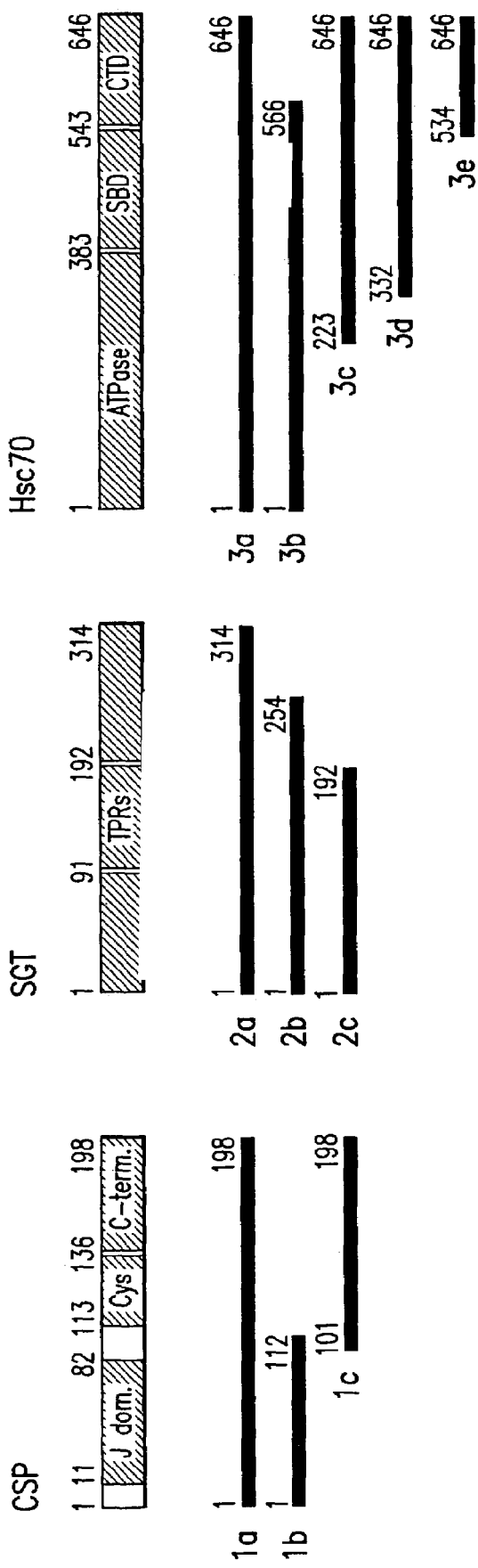
FIGS. 1A-C shows that the three proteins, CSP, SGT, and Hsc70, directly interact with each other. A. Domain structures of CSP, SGT, and Hsc70. The following abbreviations were used: Cys for a cysteine-rich cluster in CSP, TPRs for tetratricopeptide repeats in SGT, SBD for the substrate binding domain in Hsc70, and CTD for C-terminal domain. Constructs used in a yeast-two hybrid interaction assay are depicted as bars below. The numbers on top of the bars represent the N- and C-terminal amino acids of various constructs. The numbers on the left side of the bars identify individual constructs. B. The interaction of all binary combinations of CSP, SGT, and Hsc70. C. A domain model for the interactions between CSP, SGT, and Hsc70.

The synaptic nerve terminal is a complex and delicate biochemical environment. Large numbers of different proteins form sophisticated macromolecular structures that engage in highly orchestrated physiological processes, including neurotransmitter synthesis, storage, release, and reuptake or inactivation, as well as the detection of neurotransmitter-mediated signals and the transduction of these signals across the plasma membrane. In addition, numerous membrane proteins are present in the synapse in the form of ion channels, which are often linked to neurotransmitter receptors. Being comprised of proteins, many of these macromolecular structures are thus sensitive to the denaturation of these protein components, and therefore dependent upon protein synthesis or renaturation for their continued function. Any degradation of these latter processes may contribute significantly to the loss of function of the nerve terminal and ultimately to its degeneration.

In accordance with the present invention, it has been discovered that 1) cysteine string protein (CSP) forms a complex in the presynaptic nerve terminal with the heat shock protein Hsc70 and the small glutamine-rich tetratricopeptide (TPR) protein (SGT), 2) that this complex constitutes a presynaptic ATP-dependent chaperone machine that is essential in maintaining long-term synaptic function, and 3) that mice in which the CSP gene has been disrupted by insertional mutagenesis (CSP knockout mice) exhibit degeneration of lower spinal motor neurons among other neuronal cell populations, leading to ascending motor disease. These findings suggest that the proteins of this chaperone machine play a substantial role in normal synaptic function, and that alterations in the efficiency of this complex may contribute to the pathogenic events underlying various neurodegenerative diseases. These assays and models described herein are thus useful for identifying additional endogenous or environmental factors that contribute to the etiologies of these diseases, and in developing effective therapies for the prevention and/or treatment of these diseases.

The present invention relates to transgenic mice having reduced CSP activity as compared to non-transgenic mice of the same genetic strain or background. In this context, a reduction in CSP activity is defined as CSP activity of less than 50% of that present in a wild-type animal of the same strain or background, but preferably less than 80% of wild-type levels, more preferably less than 90% of wild-type levels and most preferably less than 95% of wild-type levels. In cases where less than 80% of wild-type CSP activity is present, CSP is said to be biologically inactive.

Because they exhibit such a pronounced neurodegenerative phenotype, the CSP KO mice described above are clearly useful for elucidating the pathophysiology of various neurodegenerative diseases. Such mice will also be useful to identify agents that ameliorate or potentiate neurodegenerative disorders. The CSP KO mice can also be crossed to a wide variety of genetic models for specific neurodegenerative diseases. Examples of such genetic models include, but are not limited to, those for Alper's disease, Alzheimer's disease, amyotrophic lateral sclerosis, Huntington's disease, Lewy Body diseases, motor neuron diseases, multiple system atrophy, olivopontocerebellar atrophy, Parkinson's disease, Pick's disease and related frontotemporal dementias, progressive supranuclear palsy, retinal degenerations including various forms of macular degeneration, tauopathies, and transmissible spongiform encephalopathies, where such models exist. The resulting hybrid animals will be useful for elucidating the pathophysiology of these same diseases and for developing improved treatments for these disorders. Those of ordinary skill in the art will recognize the existence of other mouse models of neurodegenerative disease that are amenable to being crossed with CSP knockout mice. Similarly, the ordinary artisan will recognize that this knockout strategy may be employed with a number of other animals, including but not limited to *Drosophila*, rats, cats, dogs, goats, sheep, pigs, primates such as macaques, chimpanzees or baboons, or any other animals species in which genetic models of neurodegenerative diseases have been recognized and characterized.

In preferred embodiments, the CSP gene of the transgenic mice has been inactivated through the deletion of a DNA fragment from the gene, through the insertion of a DNA fragment into the gene, or through the incorporation of a nonsense, missense or splicing mutation into the gene. The aforementioned DNA alterations can be made to the non-coding or coding regions of the CSP gene, provided that they decrease or reduce the ability of this gene to produce a CSP mRNA encoding a biologically active CSP protein.

The present invention also relates to transgenic mice having enhanced expression of CSP activity as compared to non-transgenic mice of the same genetic strain or background. In this context, increased or enhanced CSP activity is defined as CSP activity of at least 110% of that found in wild-type animals of the same strain or genetic background, but preferably more than 120% of wild-type levels, more preferably more than 150% of wild-type levels and most preferably at least about 200% of wild-type levels. These transgenic mice also are useful for elucidating the pathophysiology of neurodegenerative diseases, and for identifying environmental or other agents that contribute to the development and progression of these diseases.

In preferred embodiments, overexpression of the CSP gene of the transgenic mice is achieved by the insertion of a DNA fragment comprising a CSP nucleic acid encoding a biologically active CSP protein into the genomic DNA of the transgenic mice. The DNA fragment to be inserted may introduce one or more copies of an expression cassette encoding a biologically active CSP protein into the genome of the transgenic mouse, and may be introduced at a single site or at multiple sites within the genome of the host. Promoters to be incorporated into the expression cassette include those that produce constitutive, high level expression, such as the CMV, EF-1α or SRα promoters, those that produce region-neuron-specific expression, such as the CaM kinase II or rhodopsin promoters, or those that permit regulatable expression, such as the tet on or tet off promoters or the steroid-inducible GeneSwitch™ system. Other promoters that are also useful in regulating the transcription of the CSP transgene will be evident to those of ordinary skill in the art.

The present invention also relates to transgenic mice having enhanced expression of CSP in combination with enhanced levels of SGT and/or Hsc70 as compared to non-transgenic mice of the same genetic strain or background. In preferred embodiments, overexpression of these gene products in the transgenic mice is achieved as described above for the CSP protein, as are the desired degrees or increased expression of these proteins relative to the expression levels of these same proteins in mice of the same genetic background or strain.

Briefly, nucleic acids encoding biologically active CSP, SGT and Hsc70 proteins are introduced into the genomic DNA of the transgenic mice. The DNA fragment or fragments to be inserted may introduce one or more copies of an expression cassette encoding biologically active forms of these three proteins into the genome of the transgenic mouse, and may be introduced at a single site or at multiple sites within the genome of the host. Promoters to be incorporated into the expression cassettes include those that produce constitutive, high level expression, such as the CMV, EF-1α or SRα promoters, those that produce region-neuron-specific expression, such as the CaM kinase II or rhodopsin promoters, or those that permit regulatable expression, such as the tet on or tet off promoters or the steroid-inducible GeneSwitch™ system. Again, other promoters that are also useful in regulating the transcription of the CSP, SGT and Hsc70 transgenes in the transgenic mice or other animals will be evident to those of ordinary skill in the art.

Various assays may be used for the measurement of CSP function. These include, but are not limited to, those in which the ATPase activity of the CSP complex is measured, those in which the binding of ATP to CSP is monitored, those in which the refolding of a reporter protein substrate by the CSP/SGT/Hsc70 chaperone complex is determined, or those in which the association of the various components of the CSP/SGT/Hsc70 chaperone complex is examined. The existence of many alternative assays for CSP function will be evident from the teachings herein to those of ordinary skill in the art.

The present invention further provides for a method of making a transgenic mouse whose cells comprise a nucleic acid encoding a mutated CSP or expressing reduced levels of CSP as compared to wild-type levels of expression. In a preferred embodiment, this method comprises 1) introducing a DNA fragment comprising an altered CSP nucleic acid encoding a biologically inactive CSP protein or expressing reduced levels of CSP protein as compared to wild-type levels of expression into mouse embryonic stem cells under conditions whereby said DNA fragment becomes integrated into the genome of the embryonic stem cells, 2) transferring said mouse embryonic stem cells into blastocysts, 3) implanting said blastocysts into the reproductive tract of a pseudopregnant female recipient mouse, and 4) maintaining said female recipient mouse under conditions whereby transgenic offspring are produced. In practicing this method, said DNA fragment may introduce a deletion, an insertion, or a missense, nonsense or splicing mutation into the DNA encoding CSP.

The present invention further provides for a method of making a transgenic mouse whose cells comprise a nucleic acid overexpressing CSP, either alone or in combination with enhanced levels of SGT and/or Hsc70, as compared to wild-type levels of expression. In a preferred embodiment, this method comprises 1) introducing a DNA fragment or fragments comprising nucleic acids encoding biologically active CSP and/or SGT and/or Hsc70 proteins into mouse embryonic stem cells under conditions whereby said DNA fragment or fragments become integrated into the genome of the embryonic stem cells, 2) transferring said mouse embryonic stem cells into blastocysts, 3) implanting said blastocysts into the reproductive tract of a pseudopregnant female recipient mouse, and 4) maintaining said female recipient mouse under conditions whereby transgenic offspring are produced.

In practicing this method, said DNA fragment or fragments may introduce one or more copies of a expression cassettes encoding biologically active CSP and/or SGT and/or Hsc70 proteins into one or more locations within the genome of the transgenic mouse. Promoters to be incorporated into the expression cassettes include those that produce constitutive, high level expression, such as the CMV, EF-1α or SRα promoters, those that produce region-neuron-specific expression, such as the CaM kinase II or rhodopsin promoters, or those that permit regulatable expression, such as the tet on or tet off promoters or the steroid-inducible GeneSwitch™ system.

The invention also provides in vivo methods for identifying agents useful for the treatment or prevention of neurodegenerative diseases. In this context, successful treatment of a disease is defined as a reduction in the severity of a given disease symptom by at least 10% relative to untreated control animals, but preferably at least 50% relative to untreated control animals, more preferably at least 80% relative to untreated control animals, and most preferably at least 90% relative to untreated control animals. Prevention of the disease is defined as the retardation of the time of onset of the symptoms of the disease by at least 10% relative to untreated control animals, but preferably at least 50% relative to untreated control animals, more preferably at least 80% relative to untreated control animals, and most preferably at least 90% relative to untreated control animals.

In a preferred embodiment, this method comprises 1) administering a test agent to the transgenic mouse in which the expression of a biologically-active CSP protein is reduced or abolished, and 2) assessing the symptoms and progression of the neurodegenerative disorder in the transgenic mouse. An amelioration in symptoms or progression of the neurodegenerative disorder is indicative of an agent that would be useful in the treatment or prevention of a neurodegenerative disorder.

As CSP KO mice suffer from premature mortality because they exhibit an ascending paralysis that clinically resembles amyotrophic lateral sclerosis (ALS), amelioration of the phenotype can be assessed by measuring mortality curves under treatment and control conditions. In addition, assays of motor performance at a defined age could be used to measure disease progression. For example, rotorod tests which utilize a test of the ability of mice to stay on a rotating rod can be employed to measured motor performance. Furthermore, treated and control animals may be sacrificed at certain time points, and the morphology of photoreceptor synapses may be examined by histochemical or immunohistochemical methods to assess directly neurodegeneration. Other endpoints indicative of the presence or absence of neurodegeneration will be apparent to those of ordinary skill in the art.

Examples of neurodegenerative diseases that may be amenable to treatment by these agents include those in which defects in protein folding or processing have been implicated. Such diseases would be recognized by those of ordinary skill in the art, and would include, but are not limited to, Alper's Disease, Alzheimer's Disease, Amyotrophic Lateral Sclerosis, Huntington's Disease, Lewy Body Diseases, Motor Neuron Diseases, Multiple System Atrophy, Olivopontocerebellar Atrophy, Parkinson's Disease, Pick's Disease and other Frontotemporal Dementias, Progressive Supranuclear Palsy, Retinal Degenerations including various forms of Macular Degeneration, Tauopathies, and Transmissible Spongiform Encephalopathies.

The instant invention also provides in vivo methods for identifying agents that contribute to the development or progression of neurodegenerative diseases. Progression of the disease. In this context, the development of the disease is defined as an increase in the severity of a given disease symptom by at least 10% relative to untreated control animals, but preferably at least 50% relative to untreated control animals, more preferably at least 80% relative to untreated control animals, and most preferably at least 90% relative to untreated control animals. Progression of the disease is defined as a reduction in the time of onset of the symptoms of the disease by at least 10% relative to untreated control animals, but preferably at least 50% relative to untreated control animals, more preferably at least 80% relative to untreated control animals, and most preferably at least 90% relative to untreated control animals.

In a preferred embodiment, this method comprises 1) administering a test agent to the transgenic mouse in which the expression of a biologically-active CSP protein is reduced or abolished, and 2) assessing the symptoms and progression of the neurodegenerative disorder in the transgenic mouse. A worsening in symptoms or increased progression of the neurodegenerative disorder is indicative of an agent that contributes to the development of progression of the neurodegenerative disorder.

Indicators of a worsening or increased progression of neurodegeneration include, but are not limited to, increased mortality, a reduction in motor performance skills at a defined age, or morphological changes in neuronal synapses, such as those of photoreceptor cells, which may be assessed directly using various histological and immunohistochemical methods known to those of ordinary skill in the art.

The instant invention also provides in vitro methods for identifying agents that contribute to the development or progression of neurodegenerative diseases. In a preferred embodiment, this method comprises 1) contacting a cell comprising CSP, SGT and Hsc70 with an agent, 2) measuring the levels of CSP activity obtained in the presence and absence of the agent, and 3) comparing the levels CSP activity measured in the presence and absence of the agent. Decreased levels of CSP activity in the presence of the agent indicate that the agent contributes to the development or progression of neurodegenerative diseases.

The instant invention further provides in vitro methods for identifying agents useful for the treatment or prevention of neurodegenerative diseases. In a preferred embodiment, this method comprises 1) contacting a cell comprising CSP, SGT and Hsc70 with an agent known to contribute to the development or progression of the neurodegenerative disease, 2) further contacting the cell with a test agent, 3) measuring the levels of CSP activity obtained in the presence of the agent known to contribute to the development or progression of the neurodegenerative disease and in the presence or absence of the test agent, and 4) comparing the levels of CSP activity measured in the presence and absence of the test agent. Increased levels of CSP activity in the presence of the test agent relative to the levels of CSP activity in the absence of the test agent indicate that the test agent is useful for the treatment or prevention of neurodegenerative diseases.

The instant invention also provides a system for identifying agents that contribute to the development or progression of neurodegenerative diseases. In a preferred embodiment, this system comprises 1) a transgenic mouse with reduced expression of CSP relative to a non-transgenic mouse of the same strain, or a transgenic mouse with overexpression of CSP or CSP and SGT and/or Hsc70 relative to a non-transgenic mouse of the same strain, and 2) reagents for assessing the endpoints of neurodegeneration in the transgenic mouse. Such reagents include, but are not limited to, those necessary for assessing mortality, motor performance at a defined age, or morphology of neuronal synapses at various time points. These non-limited examples of neurodegeneration endpoints could be measured in the presence and absence of a given test agent. Increases in mortality, reductions in motor performance, or enhanced synaptic degeneration in the transgenic animals would be indicative of an agent that contributes to the development or progression of neurodegenerative diseases.

In another embodiment, this system for identifying agents that contribute to the development or progression of neurodegenerative diseases comprises 1) cells expressing CSP, SGT and HSC70, and 2) reagents for assessing the consequences of this expression on cellular processes implicated in neurodegeneration, such as protein folding. Alternatively, the CSP-, SGT, and Hsc70-expressing cells could further express a protein whose expression or overexpression has been implicated in various neurodegenerative states. Examples of such proteins include, but are not limited to, mutant forms of synuclein or the wild-type or mutant forms of the amyloid precursor protein (APP). Agents that contribute to the development or progression of neurodegenerative diseases would include those that reduce or prevent the proper folding of a reporter protein, such as luciferase, in these cells, or that enhance the known consequences of toxicity associated with the co-expression of proteins implicated in various neurodegenerative diseases, for example the measurement of levels of Aβ40 and Aβ42 production from cells in which CSP, SGT, and Hsc70 are co-expressed in combination with APP.

The instant invention also provides a system for identifying agents that are useful for the treatment or prevention of neurodegenerative diseases. In a preferred embodiment, this system comprises 1) a transgenic mouse with reduced expression of CSP relative to a non-transgenic, animal of the same strain, or a transgenic animal with overexpression of CSP or CSP and SGT and/or Hsc70 relative to a non-transgenic, animal of the same strain, and 2) reagents for assessing the endpoints of neurodegeneration. Such reagents include, but are not limited to, those necessary for assessing mortality, motor performance at a defined age, or morphology of neuronal synapses at various time points. These non-limited examples of endpoints of neurodegeneration could be measured in the presence and absence of a given test agent. Reductions in mortality, increases in motor performance, or reduced synaptic degeneration in the transgenic animals would be indicative of an agent that is useful for the treatment or prevention of neurodegenerative diseases.

In another embodiment, this system for identifying agents that are useful for the treatment or prevention of neurodegenerative diseases comprises 1) cells expressing CSP, SGT and HSC70, and 2) reagents for assessing the consequences of this expression on cellular processes implicated in neurodegeneration, such as protein folding. Alternatively, the CSP-, SGT, and Hsc70-expressing cells could further express a protein whose expression or overexpression has been implicated in various neurodegenerative states. Examples of such proteins include, but are not limited to, mutant forms of synuclein or the wild-type or mutant forms of the amyloid precursor protein (APP). Agents that agents that are useful for the treatment or prevention of neurodegenerative diseases would include those that enhance the proper folding of a reporter protein, such as luciferase, in these cells, or that reduce or abolish the known consequences of toxicity associated with the co-expression of proteins implicated in various neurodegenerative diseases, for example the measurement of levels of Aβ40 and Aβ42 production from cells in which CSP, SGT, and Hsc70 are co-expressed in combination with APP.

The following nonlimiting examples serve to further illustrate the present invention.

EXAMPLES

Experimental Procedures cDNA Cloning, Construction of Expression Vectors, Sequencing, Expression of Recombinant Proteins. Full-length cDNAs for rat CSP1 and Hsc70 were generated by polymerase chain reaction (PCR) using primers specific for the respective 5'- and 3'-ends of their coding regions and rat brain cDNA (BD Biosciences Clontech, Palo Alto Calif.) as template. For amplification by PCR, Pfu polymerase (Stratagene, La Jolla Calif.) was used. The PCR products were subcloned into pGEX-KG (Guan and Dixon, 1991, *Anal. Biochem.* 192:262-267) using restriction enzyme sites placed into the oligonucleotide sequences. A partial sequence of SGT obtained by a yeast two-hybrid screen was used as probe to screen a rat brain cDNA library in λZAP II at high stringency. Yeast bait vector constructs were generated by subcloning of CSP1 and SGT cDNA into pLexN (Vojtek et al., 1993, *Cell* 74:205-214). Prey vector constructs for Hsc70 and SGT were obtained by subcloning of PCR fragments into pVP16 (Vojtek et al., 1993, *Cell* 74:205-214). His$_6$-tagged Hsc70 and SGT were created by cloning the respective BamHI/NotI fragments into pET-28a (Novagen, Madison Wis.). A Semliki Forest Virus construct encoding full-length SGT in-frame with EGFP was constructed by cloning of a blunt-end SGT-EGFP cDNA into the SmaI site of pSFV1 (GIBCO-BRL). The identity of most DNA constructs was confirmed by sequencing. GST-tagged fusion proteins were expressed in *Escherichia coli* (strain XL1-Blue) and purified according to a standard procedure (Smith and Johnson, 1988, *Gene* 67:31-40). His$_6$-tagged fusion proteins were expressed in the *E. coli* strain BL21(DE3) and purified as described (Noji et al., 1997, *Nature* 386:299-302).

Yeast Two-Hybrid Screen and Interaction Assay. Yeast strain L40 (Vojtek et al., 1993, *Cell* 74:205-214) was sequentially transfected with the bait vector (full-length rat CSP cloned into pLexN) and a rat brain cDNA library (Vojtek et al., 1993, *Cell* 74:205-214) using lithium acetate (Schiestl and Gietz, 1989, *Curr. Genet.* 16:339-346). All the following steps were performed as described (Stahl et al., 1999, *Eur. J. Cell Biol.* 78:375-381).

Gel Filtration. Proteins bound to immobilized GST/CSP on glutathione beads were eluted with 25 mM glutathione in 0.2 M Tris (pH 8.0). Following centrifugation at 100,000×g for 10 min, the eluate was subjected to gel filtration on a FPLC Superose 6 column (Pharmacia) according to the instructions of the manufacturer. When indicated, the column run was performed in the presence of 1 mM ADP and ATP, respectively. Thirty fractions with a fraction size of 1.8 ml were obtained. To increase the protein concentration for a subsequent SDS gel electrophoresis, fractions were concentrated 25-fold using a standard procedure.

In Situ Hybridization. Male Wistar rats (8 weeks old) were anaesthetized and decapitated. All the following steps were performed as described (Augustin et al., 1999, *Biochem. J.* 337:363-371). Antisense oligonucleotides representing the following sequences were chosen as probes: bp 37-81/466-510 of CSP (GenBank Accession Number S81917); bp 1040-1084/1335-1379 of Hsc70 (GenBank Accession Number X70065); bp 226-270/612-656 of SGT (GenBank Accession Number AJ222724).

Determination of Hsc70 ATPase Activity. Hsc70 ATPase activity was assayed with minor modifications as described (Braun et al., 1996, *Neuropharmacology* 34:1361-1369). In brief, the rate of ATP hydrolysis was analyzed after incubation of 0.5 μM GST/Hsc70 with 0.5 μM GST/CSP and 0.5 μM GST/SGT in 100 mM Tris (pH 8.4), 100 mM KCl, 0.5 mM DTT, 2 mM MgCl$_2$, 5 nM [α-$^{32}$P] ATP (20 mCi/mmol) for the indicated times at 37° C. Afterwards, radioactive nucleotides were separated by thin layer chromatography on PEI cellulose and analyzed with a PhosphorImager (Fuji).

Luciferase Refolding Assay. Firefly luciferase (Boehringer Mannheim) was denatured at a concentration of 3 μM in 6 M guanidinium-HCl, 30 mM Tris (pH 7.4), 3 mM DTT at 25° C. for 1 hr. The unfolded protein was diluted 100-fold into 10 mM MOPS (pH 7.2), 50 mM KCl, 3 mM MgCl$_2$, 5 mM DTT containing approximately 0.5 μM His$_6$-SGT, 0.5 μM GST/CSP, 0.5 μM His$_6$-Hsc70 and 1 mM ATP when indicated. Luciferase activities were measured after 1 hr incubation at 30° C.

Generation and Maintenance of CSP Knockout Mice. A knockout vector was constructed from a mouse genomic CSP clone. Exon 1 and flanking introns were replaced by a neomycin resistance gene cassette (see FIG. 3A). Embryonic stem cells were electroporated with the vector and selected with G418 (Life Technologies, Inc.) and FIAU essentially as described (Rosahl et al., 1993, *Cell* 75:661-670). Resistant embryonic stem cell clones were analyzed by polymerase chain reaction for homologous recombination. Positive clones were injected into blastocysts, resulting in the generation of a single mouse line that was bred to homozygosity.

Hippocampal Neuron Culture and Electrophysiology. Microisland culture preparation of hippocampal neurons was performed according to a modified version of published procedures (Bekkers and Stevens, 1991, *Proc. Natl. Acad. Sci. USA* 88:7834-7838). After 10-14 days in culture, cells were infected with 50 µl of an activated Semliki Forest virus containing the cDNA of full-length SGT coupled to green fluorescent protein (GFP) at its C-terminal end. All measurements were performed 12 to 18 hours after infection. Only dots containing a single neuron forming excitatory synapses (autapses) were used. Data are expressed as mean±standard error. Statistical significance was tested by Mann-Whitney U test.

Antibodies and Immunohistochemical Procedures. Polyclonal rabbit and mouse antibodies directed against rat CSP and SGT were generated with GST fusion proteins containing full-length constructs of both proteins. A goat antibody against Hsc70 was purchased from Santa Cruz Biotechnology (Santa Cruz Calif.), and a mouse antibody specific for the $His_6$ epitope was from Qiagen (Valencia Calif.). Antibodies to GDI (GDP dissociation inhibitor, cl. 81.2), synaptophysin (cl. 7.2), synaptotagmin (cl. 604.4), synaptobrevin (cl. 69.1), syntaxin (cl. 78.2 and R31), SNAP25 (cl. 71.1 and R28), NSF (cl. 83.1), rabphilin (I734), and rab3A (cl. 42.2 and R9) were kindly provided by Dr. R. Jahn (Max Planck-Institute for Biophysical Chemistry, Göttingen, Germany).

Immunofluorescence analyses of retinal sections was performed as described previously (; von Kriegstein et al., 1998, *Eur. J. Neurosci.* 11:1335-1348; Schmitz et al., 2000, *Neuron* 28:857-872).

Miscellaneous Procedures and Materials. All chemicals were of the highest available purity and were purchased from standard sources. SDS-polyacrylamide gel electrophoresis and immunoblotting were performed with minor modifications as described (Laemmli, 1970, *Nature* 227:680-685; Towbin et al., 1979, *Proc. Natl. Acad. Sci. USA*, 76:4350-4354). Immunoprecipitation of synaptic proteins was performed as described (Stahl et al., 1996, *EMBO J.* 15:1799-1809). Immunoreactive bands were visualized with enhanced chemiluminescence (Amersham Corp.). Subcellular fractionation of brain tissue was done according to a standard procedure (Walch-Solimena et al., 1995, *J. Cell Biol.* 128: 637-645).

Example 1

A Yeast Two-Hybrid Screen for CSP Identifies a Novel Binding Partner. A yeast two-hybrid screen was performed with rat CSP1 using a rat brain library as source of preys. Eighty-five million yeast double transformants were screened for interaction with CSP1 (Vojtek et al., 1993, *Cell* 74:205-214). Among the clones isolated in the screen, 29 were found to be positive in a β-galactosidase assay. Sequencing revealed that 24 clones represented partial clones of a single protein with tetratricopeptide repeats (TPRs). This protein was discovered recently because of its putative interaction with two viruses, i.e. human immunodeficiency virus type 1 and parvovirus H-1 (Callahan et al., 1998, *J. Virol.* 72:5189-5197; Cziepluch et al., 1998, *J. Virol.* 72:4149-4156). Due to its domain structure, it was termed SGT, an abbreviation for small glutamine-rich TPR protein.

In the yeast two-hybrid screen, 24 positive clones encoding partial SGT were identified, the longest of which encoded 81% of the SGT protein (FIG. 1A, construct 2b). Screening of a rat brain cDNA library in λZAP II using a partial yeast clone as probe resulted in the cloning of a full-length SGT. The heat-shock protein cognate Hsc70, a known binding partner for CSP, was found in a previous yeast-two hybrid screen using the J domain of CSP as bait (data not shown).

Figure 1B:
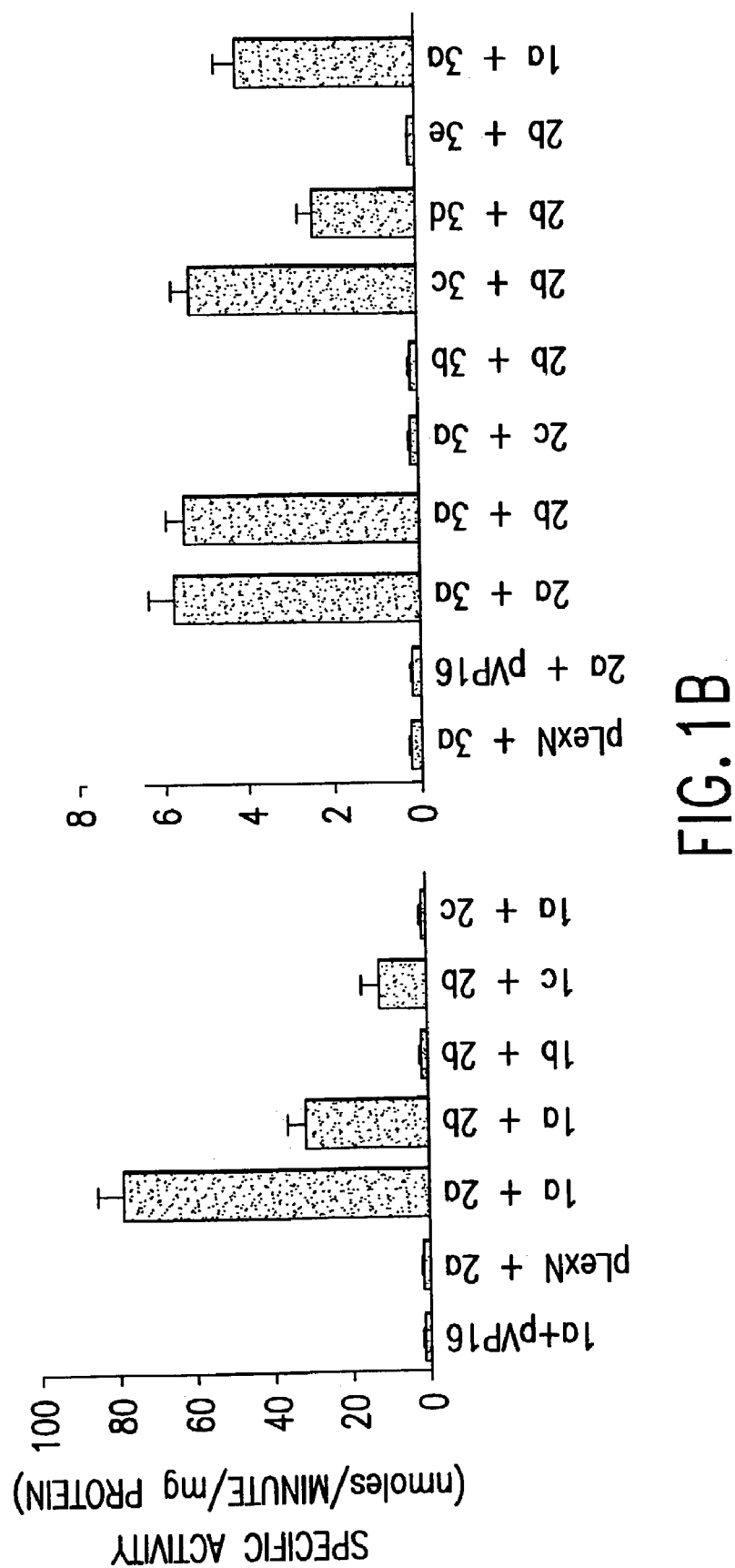

The interaction of all binary combinations of CSP, SGT, and Hsc70 was determined by measuring the specific activity of the reporter gene β-galactosidase. β-galactosidase activity was measured in triplicates and is shown as the mean±SD. These studies confirmed that the activation of the reporter gene β-galactosidase depended on both proteins, i.e. CSP1 and SGT (FIG. 1B, left diagram, cf. columns 1-3). CSP directly interacts with SGT (FIG. 1B, left diagram, column 3). This interaction is mediated by the C-terminal half of CSP (FIG. 1B, left diagram, column 6). SGT also interacts with Hsc70 (FIG. 1B, right diagram, column 3). For this interaction, the C-terminal domain of Hsc70 is essential (FIG. 1B, right diagram, column 6). As previously reported, CSP also binds to Hsc70 (FIG. 1B, right diagram, column 10). Combinations of CSP1 and SGT, respectively, with prey and bait vectors devoid of inserts, i.e. pVP16 and pLexN, did not result in a β-galactosidase activation (FIG. 1B, left diagram, columns 1 and 2).

CSP2, a splice variant of CSP1 differing at the C terminus (Chamberlain et al., 1996, *J. Biol. Chem.* 271:19514-19517), was also examined to determine if it could bind to SGT. A similarly strong interaction was found (data not shown). As shown in FIG. 1B (left diagram, column 5), the C-terminal domain of CSP is essential for binding to SGT, whereas the N-terminal J domain is not necessary. For the interaction with CSP, the TPRs in SGT are necessary but not sufficient (FIG. 1B, left diagram, column 7).

Example 2

SGT Directly Interacts with CSP and Hsc70. Several proteins with TPRs are known to interact specifically with heat-shock proteins, e.g. Hip and Hop bind to Hsc70 and immunophilins and phosphoprotein phosphatase 5 (PP5) interact with Hsp90 (Hohfeld et al., 1995, *Cell* 83:589-598; Young et al., 1998, *J. Biol. Chem.* 273:18007-18010). Since these interactions are mediated by the TPRs, the possibility existed that SGT binds to Hsc70 via its TPRs. Using the yeast two-hybrid retransformation assay, such an interaction was confirmed (FIG. 1B, right diagram, columns 3 and 4). The TPRs of SGT are necessary but not sufficient for binding of Hsc70 (FIG. 1B, right diagram, column 5). Interestingly, the C-terminal domain but not the ATPase domain of Hsc70 is essential for the interaction with SGT (FIG. 1B, right diagram, columns 7 and 8). The specificity of the SGT/Hsc70 interaction is further underlined by the observation that other heat-shock proteins like Hsp60 and Hsp90 did not interact with SGT (data not shown). The strength of interaction between SGT and Hsc70 is one order of magnitude smaller than that of SGT and CSP (compare the y-axes of FIG. 1B, both diagrams). However, it is on the same order of magnitude as that of CSP and Hsc70 (FIG. 1B, right diagram, column 10).

Figure 1C:
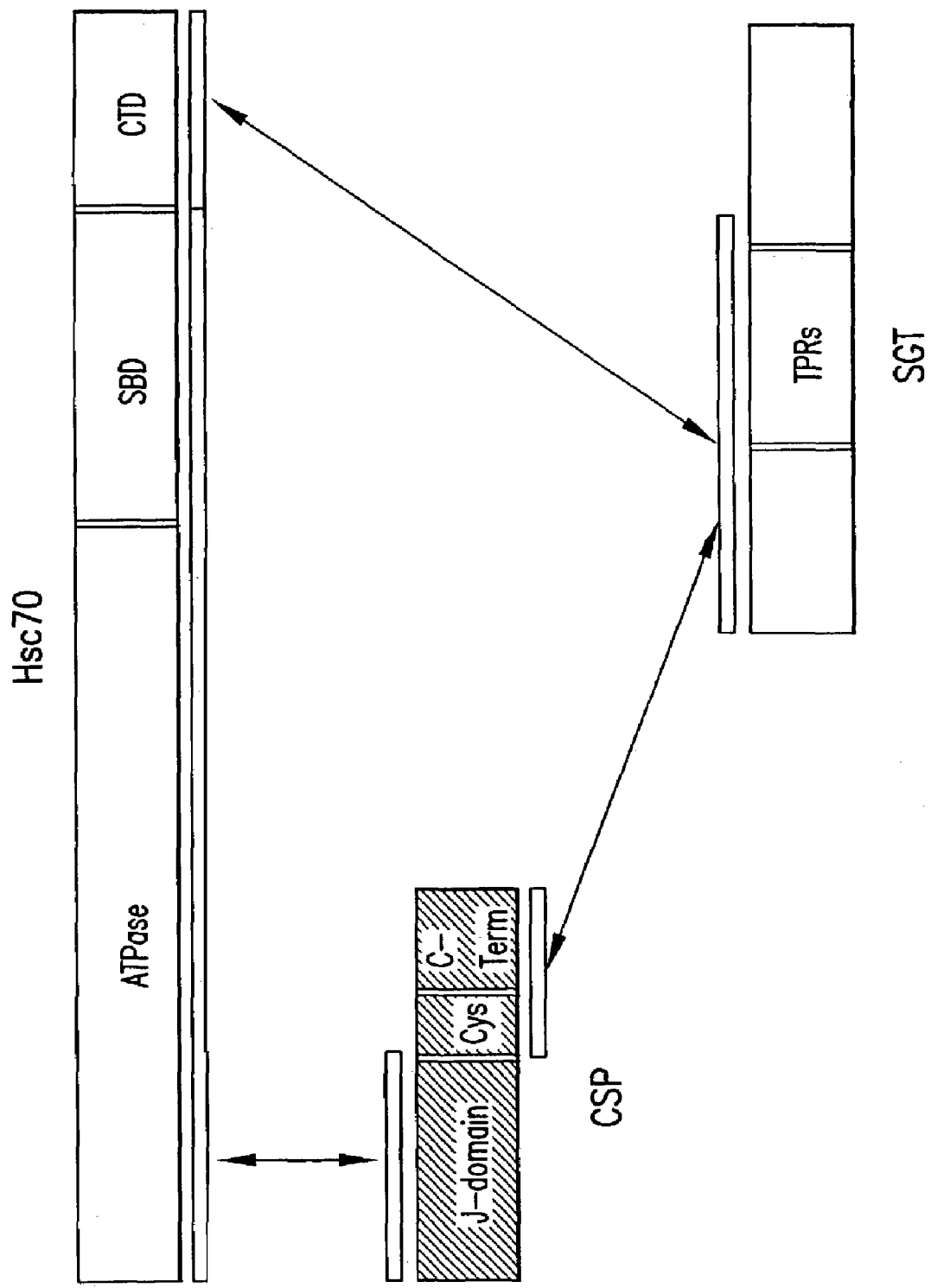

These data strongly support the idea that CSP, Hsc70, and SGT can bind to each other. The domains involved in these interactions are depicted in the model shown in FIG. 1C. The J domain of CSP is essential for the interaction with Hsc70 (Braun et al., 1996, *Neuropharmacology* 34:1361-1369), whereas the C-terminal domain of CSP mediates the binding of SGT. The cooperation of two distinct domains in Hsc70, i.e. the ATPase domain and the substrate binding domain, is necessary and sufficient for interaction with CSP (Stahl et al., 1999, *Eur. J. Cell Biol.* 78:375-381). In contrast, the C-terminal domain but not the ATPase domain of Hsc70 is crucial for binding of SGT. The TPRs of SGT are essential for the binding of both CSP and Hsc70.

Example 3

CSP, Hsc70, and SGT Form a Trimeric Complex In vitro. The data from the yeast two-hybrid studies described above predicted that CSP, Hsc70, and SGT might form dimeric and/or trimeric complexes under certain conditions (see FIG. 1C). This possibility was checked by incubating recombinant SGT or Hsc70 with immobilized CSP or Hsc70. In these studies, GST fusion proteins of full-length CSP and Hsc70, respectively, were immobilized on glutathione beads. These beads were incubated with His6-SGT or His6-Hsc70 in the presence of either ADP or ATP. Proteins bound to these beads were analyzed by SDS-PAGE and immunoblotting for the His6 epitope.

Figure 2A:
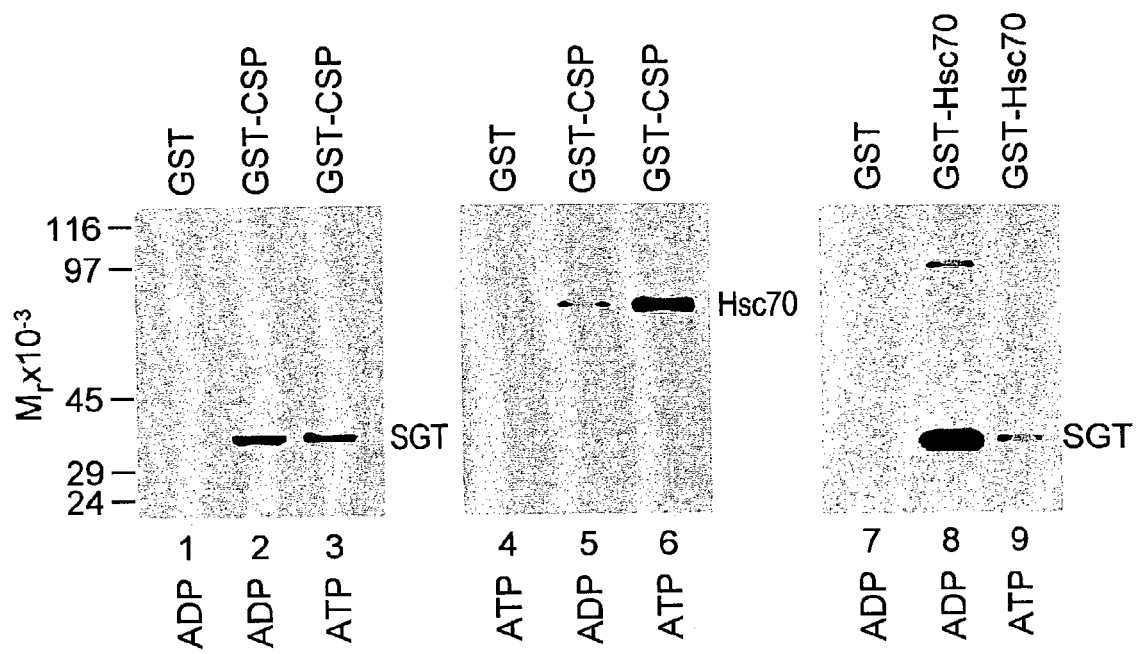
FIGS. 2A-C shows that CSP, SGT and Hsc70 form a trimeric complex in the presence of ADP. A. The formation of dimeric complexes between CSP, SGT, and Hsc70 was analyzed. SGT specifically interacted with CSP (lanes 2 and 3), whereas GST alone did not interact (lane 1). Hsc70 bound in an ATP-dependent manner to CSP (lane 6), while SGT interacted with Hsc70 in the presence of ADP (lane 8). B. A GST fusion protein of full-length CSP was incubated with a combination of His6-SGT and His6-Hsc70. In the presence of ADP, Hsc70 and SGT interacted with CSP (lane 2). ATP prevented the formation of a protein complex (lane 3), and induced a dissociation of both components of the complex (lane 5). C. The complex consisting of GST/CSP, SGT, and Hsc70 was assembled on glutathione beads in the presence of ADP.

SGT interacted with CSP in a nucleotide-independent manner (FIG. 2A, lanes 2 and 3). In contrast, Hsc70 bound to CSP more strongly in the presence of ATP than ADP (FIG. 2A, lane 5). Conversely, the third dimeric interaction, the interaction between SGT and Hsc70, depended on ADP (FIG. 2A, lane 8).

Figure 2B:
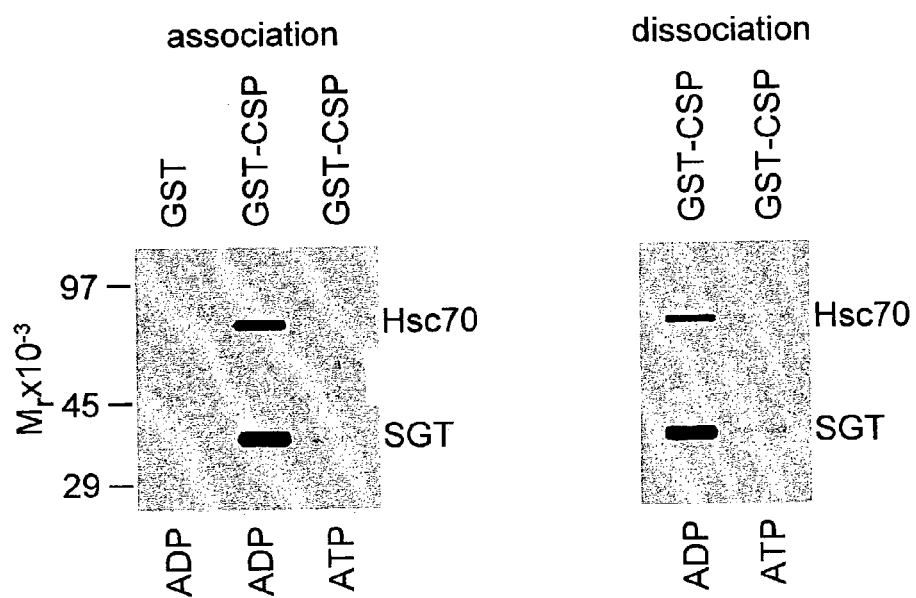

These results demonstrated that CSP, Hsc70, and SGT could bind to each other, but did not define the conditions under which these proteins could assemble to form the trimeric complex. This question was addressed by incubating both Hsc70 and SGT with immobilized CSP in the presence of ADP or ATP. Both proteins, Hsc70 and SGT, were found on CSP-beads in the presence of ADP, while ATP abolished the interaction (FIG. 2B, lanes 2 and 3). The preformed complex could be dissociated by incubation with ATP, but not by ADP (FIG. 2B, lanes 4 and 5).

This observation can be explained by two hypotheses—either two dimeric complexes of CSP/Hsc70 and CSP/SGT formed in equal amounts or a trimeric complex consisting of CSP, Hsc70, and SGT assembled. The fact that incubation with ATP resulted in a dissociation of both proteins, Hsc70 and SGT, and not only of Hsc70, strongly supports the second hypothesis. This hypothesis was tested by studying the behavior of the complex on a gel filtration column (Superose 6).

In these studies, the CSP/SGT/Hsc70 complex was eluted from the beads by incubation with glutathione, and subjected to gel filtration in the presence of ADP. Two separate column runs were performed. As a negative control, beads depleted of Hsc70 and SGT were used. As a further control, the same experiment was performed using ATP instead of ADP. In both cases, the beads were extensively washed. Proteins were then eluted by addition of glutathione and subjected to gel filtration on a Superose 6 column. Fractions were collected and analyzed by immunoblotting.

Figure 2C:
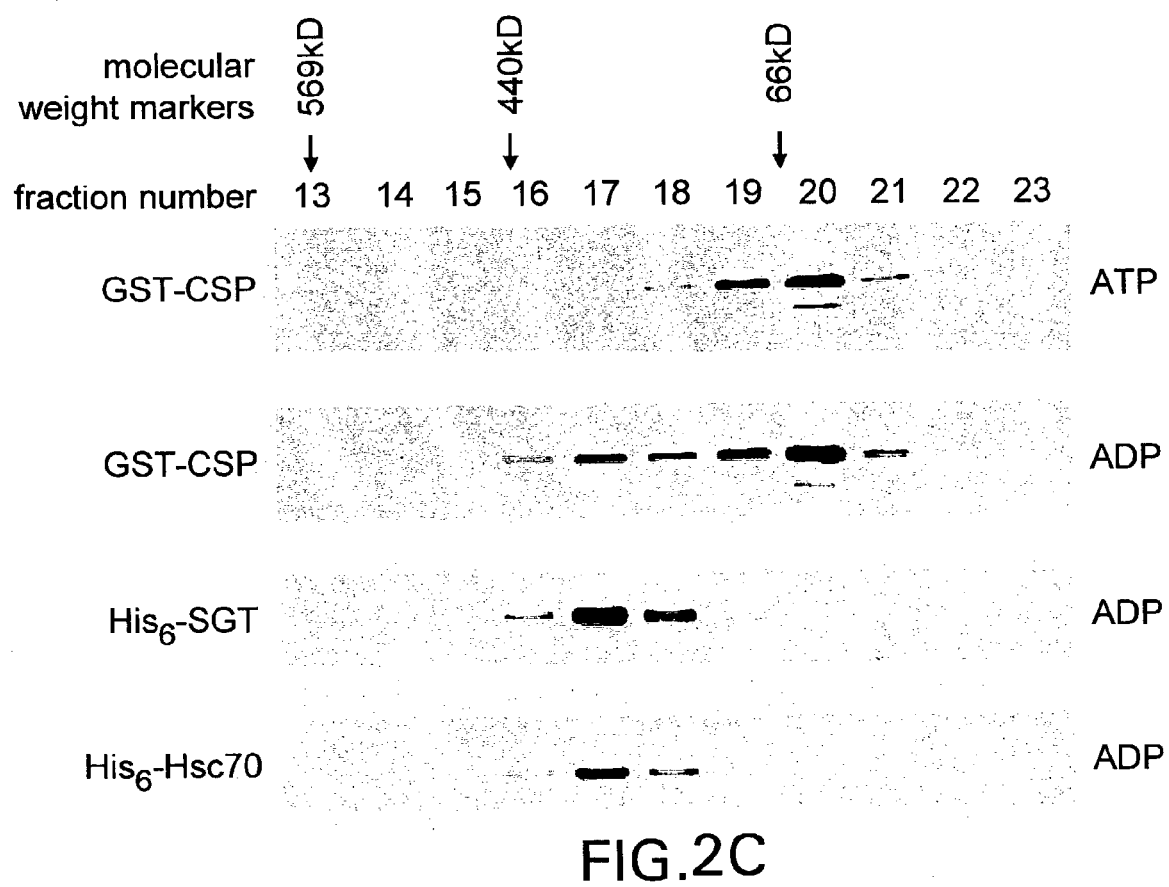

Upon gel filtration, GST/CSP from the control beads eluted at a size of 18 50 kDa (FIG. 2C, first panel). In a second column run, proteins from the assembled complex were analyzed. To avoid a disassembly of the complex, ADP was added to the running buffer. This time, a substantial part of GST/CSP shifted to a molecular weight of ~300 kDa (FIG. 2C, second panel). Consistent with the hypothesis of a trimeric complex, GST/CSP, SGT, and Hsc70 eluted at the same size (~300 kDa). This molecular weight is twice the size as expected, suggesting that the stoichiometry of the trimeric complex is 2:2:2 rather than 1:1:1.

Example 4

Figure 3A:
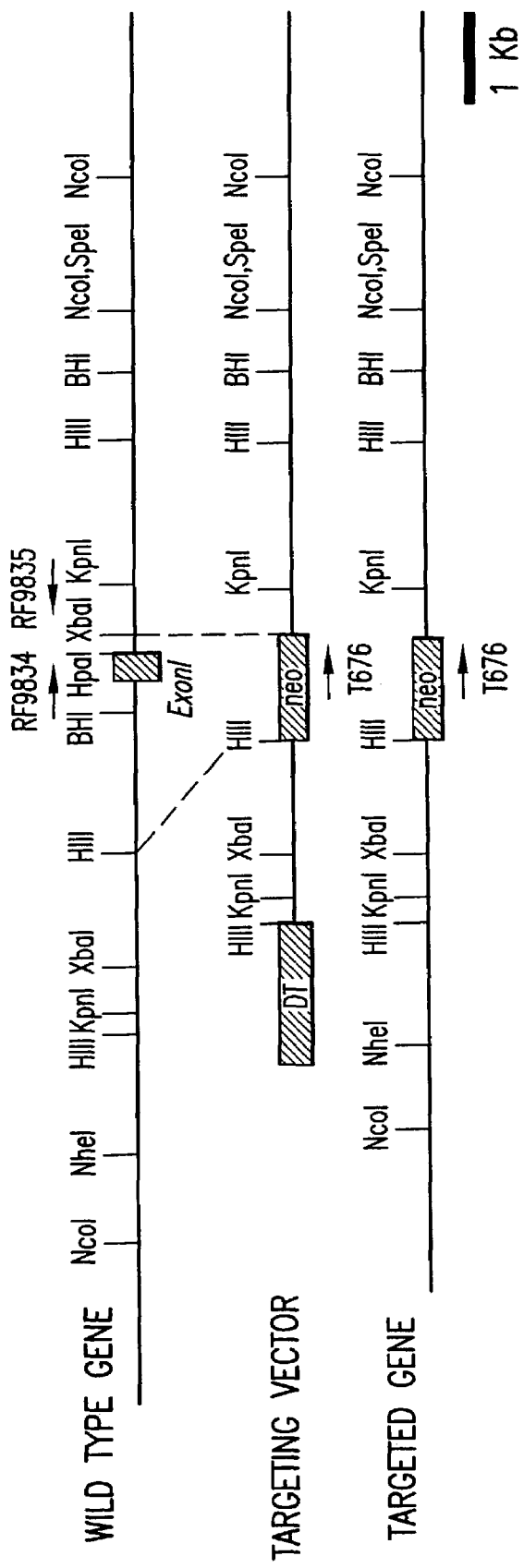
FIGS. 3A-C. Creation and screening of a CSP knockout (KO) mouse. A. Schematic diagram of the strategy utilized for the creation of the CSP KO mouse. B. PCR-based genotyping of homozygous normal mice (+/+), heterozygous CSP KO mice (+/−) and homozygous CSP KO mice (−/−). C. Western-based genotyping of homozygous normal mice (+/+), heterozygous CSP KO mice (+/−) and homozygous CSP KO mice (−/−).
Figure 3B:
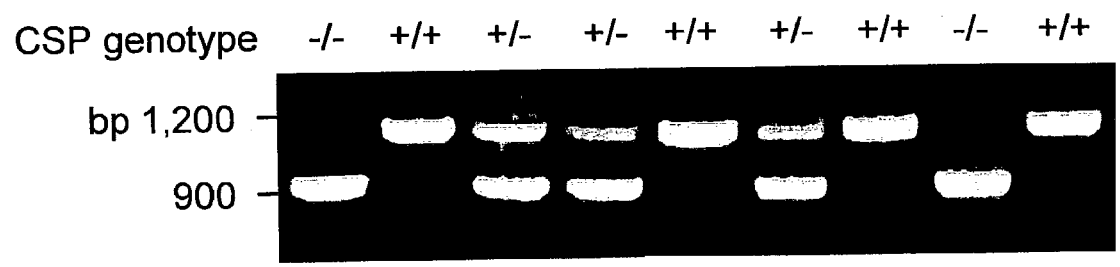
Figure 3C:
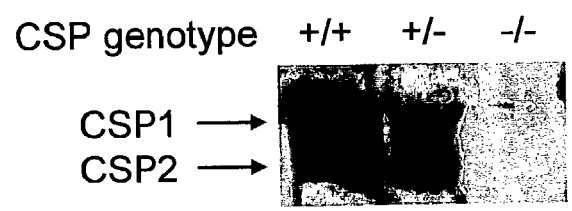

Generation and Characterization of CSP Knockout Mice. To further examine the role of CSP in synaptic function, transgenic mice were created in which the CSP locus was inactivated by insertional mutagenesis using techniques well known to those skilled in the art and as previously described (Rosahl et al, 1993, *Cell* 75:661-670; Geppert et al., 1994, *EMBO J.* 13:3720-3727). Restriction maps of the wild-type mouse CSP gene, the CSP targeting vector, and the resulting inactivated CSP gene are shown in FIG. 3A. Also indicated in FIG. 3A are the relative locations of three primers, RF9834, RF9835 and T676, which were employed in a PCR-based assay designed to detect the wild-type CSP gene or the disrupted version of this gene. In this assay, the amplification of an approximately 1,200 bp fragment by primer pairs RF9834 and RF9835 was indicative of the wild-type CSP gene, while amplification of an approximately 1,200 bp fragment by primer pairs T676 and RF9835 was indicative of the disrupted CSP gene. Wild-type, heterozygous CSP KO and homozygous CSP KO animals could be readily discerned by this assay (FIG. 3B). A Western-based assay, using a polyclonal rabbit anti-rat CSP antibody (Tobaben et al., 2001, *Neuron* 31:987-99), could also discriminate between these three populations, although the use of this antibody was complicated somewhat by its cross-reactivity with CSP 2 (FIG. 3C). These studies confirmed the insertion of the neo gene into the CSP locus (FIG. 3B), resulting in a nearly complete loss of expression of CSP1 and CSP2 (FIG. 3C).

Figure 4A:
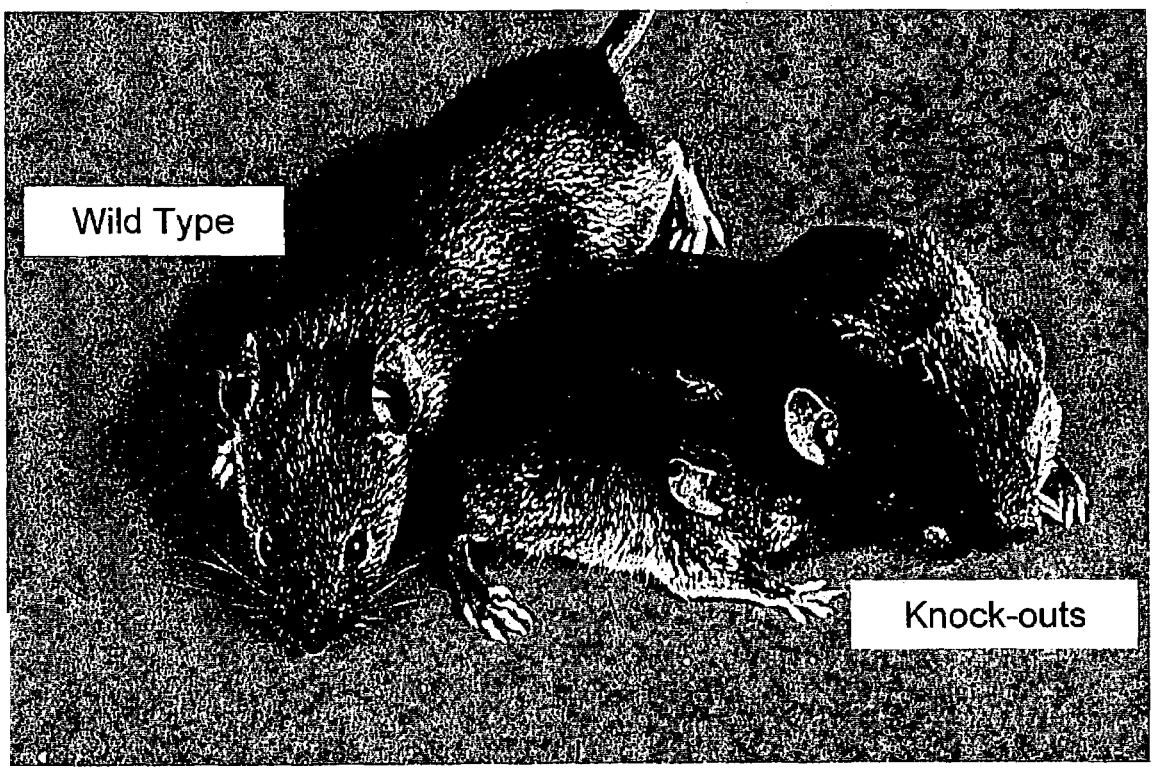
Figure 4C:
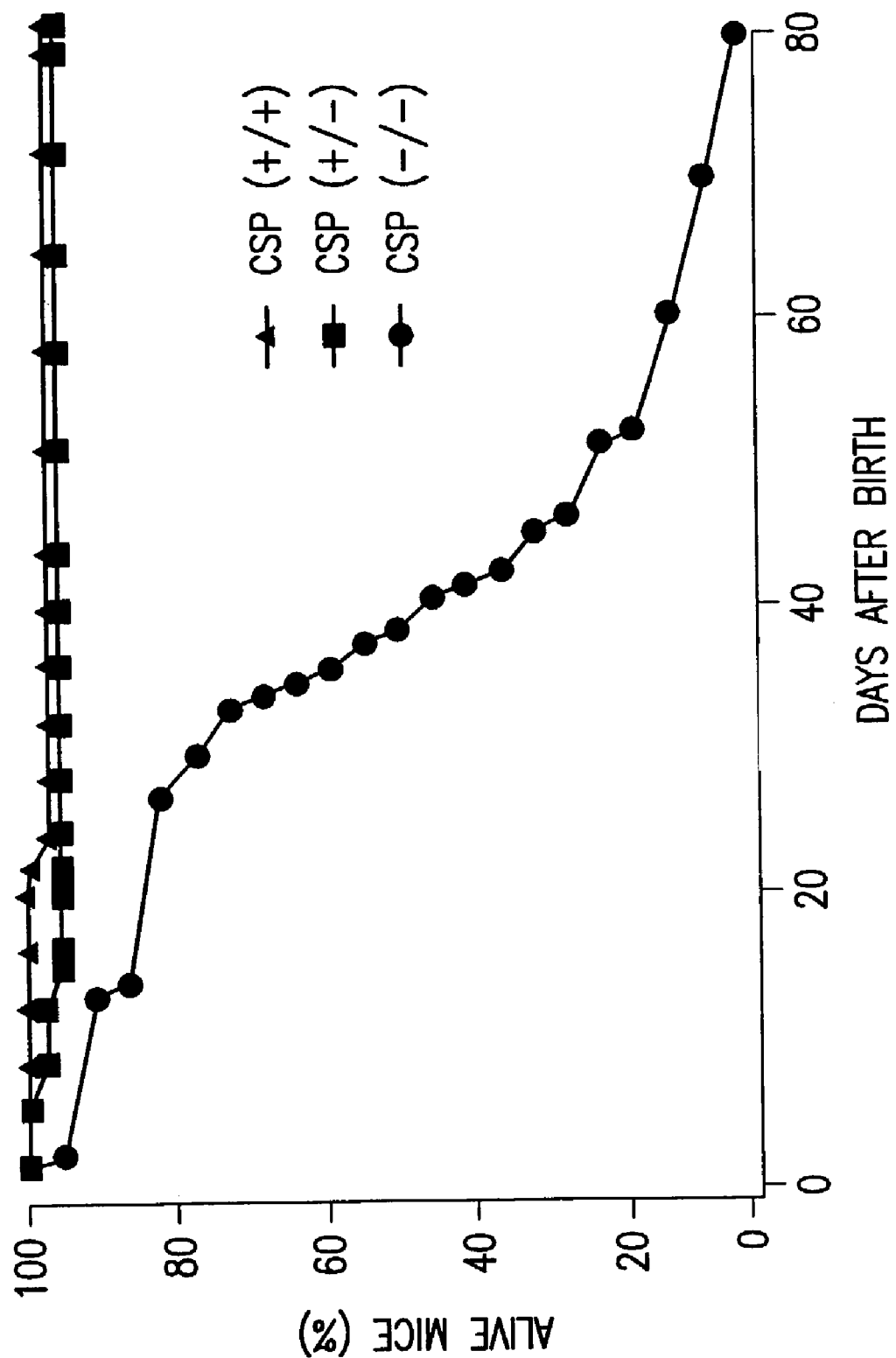

Wild-type and CSP KO mice are shown in FIG. 4A. CSP mice are apparently healthy at birth, and their increase in body weight is virtually indistinguishable from heterozygous CSP KO or homozygous wild-type animals over the first two weeks after birth (FIG. 4B). However, by three weeks postpartum, weight gain in the homozygous CSP KO mice plateaus (FIG. 4B), and a significant proportion of animals begin to die (FIG. 4C). Approximately half of the homozygous CSP KO mice are dead within 40 days of birth, and none survive more than three months (FIG. 4C).

Figure 5A:
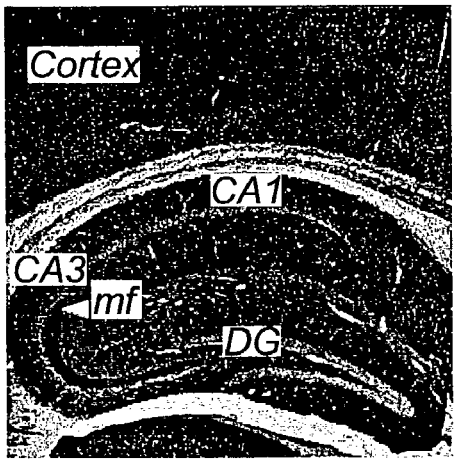
FIGS. 5A-C shows the immunohistochemical staining of CSP in hippocampal sections from homozygous wild-type (A) and homozygous CSP KO (B) mice. The immunohistochemical staining of the synaptic protein synaptoporin in hippocampal sections from homozygous CSP KO mice (C) is included as an alternative to structural visualization to confirm normal hippocampal structure in the CSP KO mice.
Figure 5B:
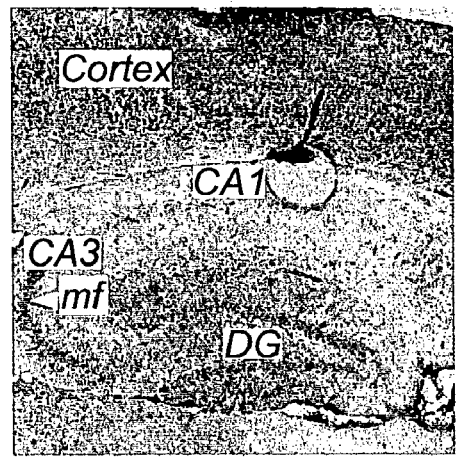
Figure 5C:
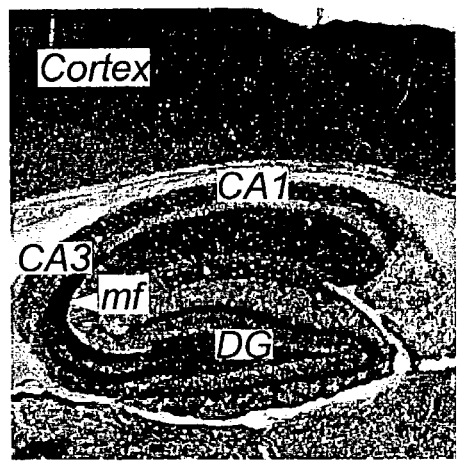
Figure 6G:
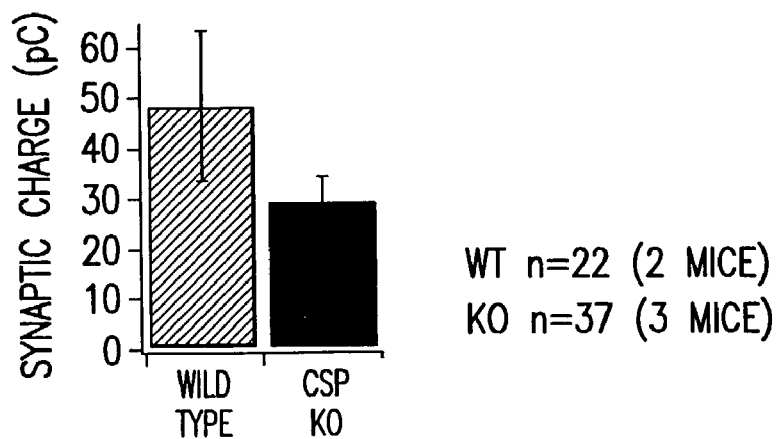
Figure 6H:
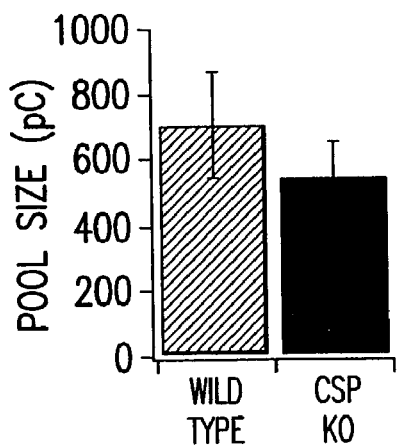
Figure 6I:
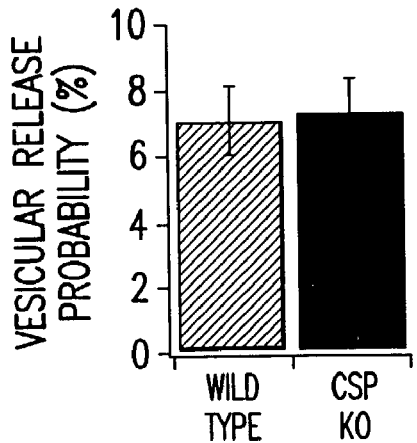
Figure 7A:
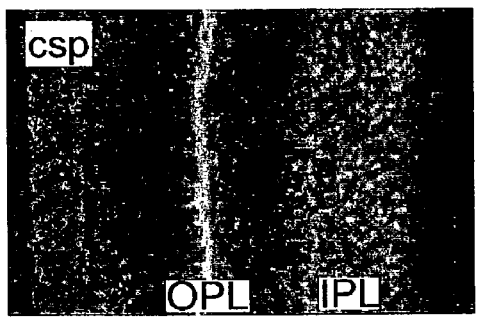
FIGS. 7A-V shows the immunohistochemical staining of CSP (A, B), Bella, a non-protein component of synaptic ribbons, (C, D), Ribeye (U2656) (E, F), Rab3 (42.1) (G, H), rhodopsin (I, J), SV2 (K, L), PSD95 (M, N), synaptophysin (O, P), NCAM (Q, R), synaptotagmin (V216) (S, T) and synaptobrevin (69.1) (U, V) in retinal sections from homozygous wild-type (A, C, E, G, I, K, M, O, Q, S, U) and homozygous CSP KO (B, D, F, H, J, L, N, P, R, T, V) mice.
Figure 7B:
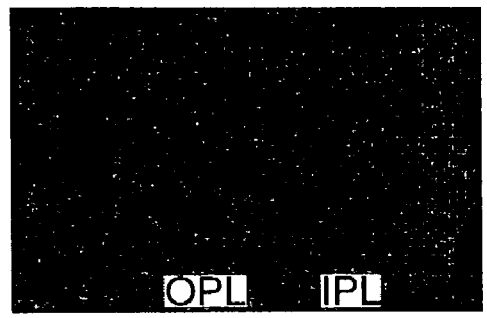
Figure 7C:
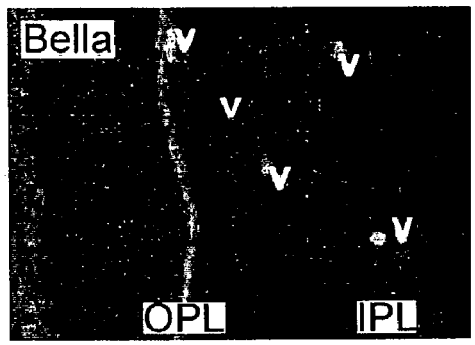
Figure 7D:
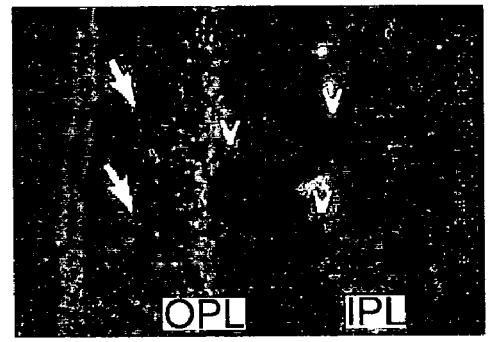
Figure 7E:
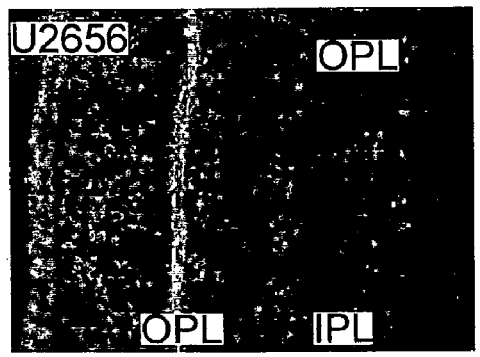
Figure 7F:
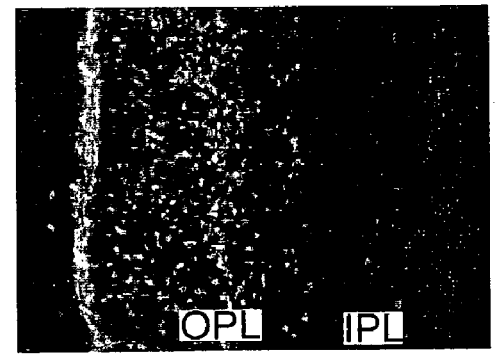
Figure 7G:
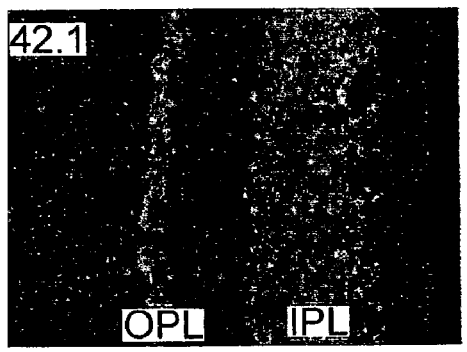
Figure 7H:
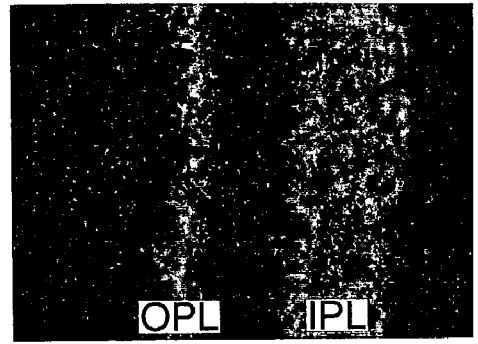
Figure 7I:
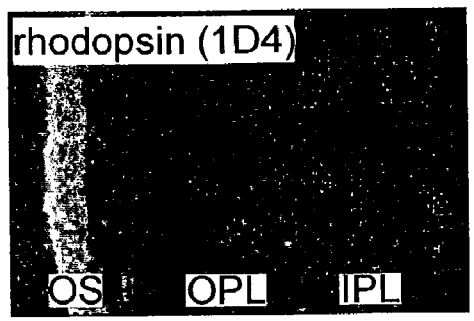
Figure 7J:
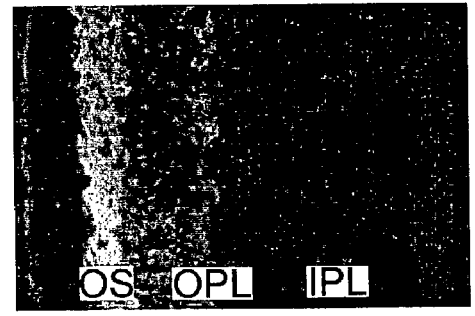
Figure 7K:
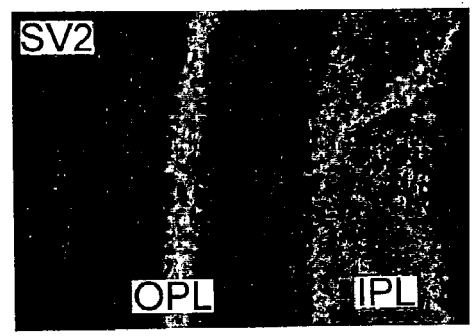
Figure 7L:
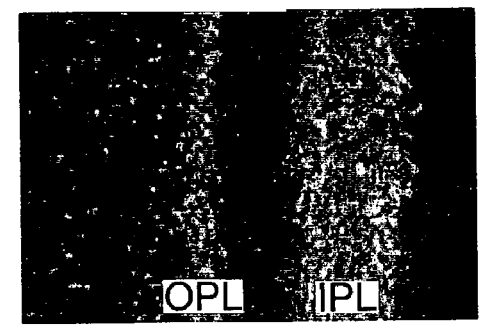
Figure 7M:
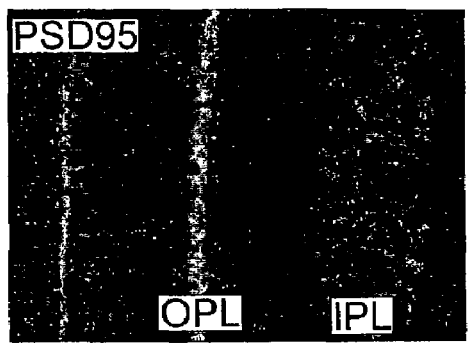
Figure 7N:
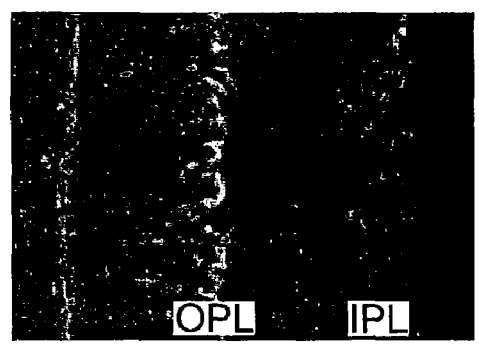
Figure 7O:
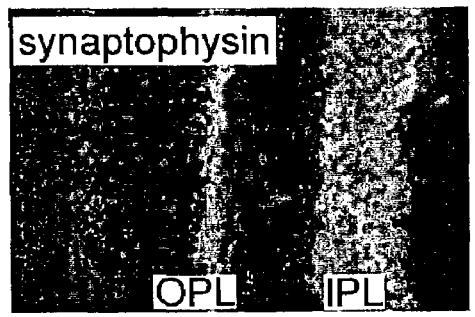
Figure 7P:
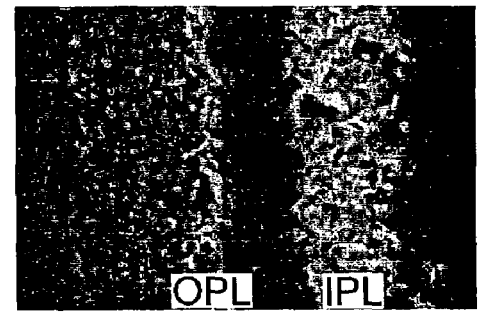
Figure 7Q:
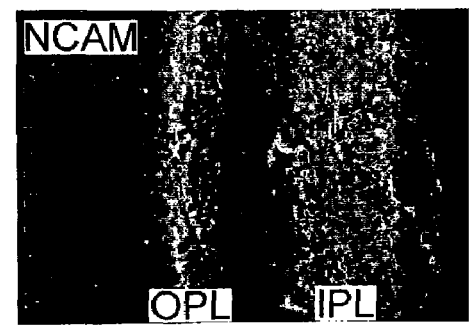
Figure 7R:
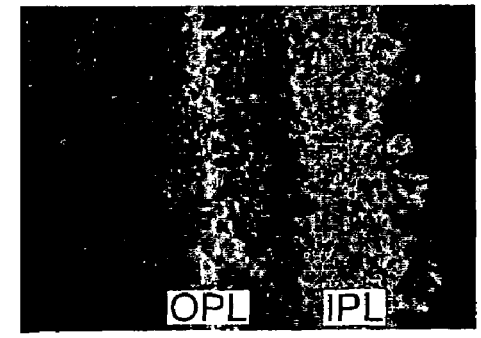
Figure 7S:
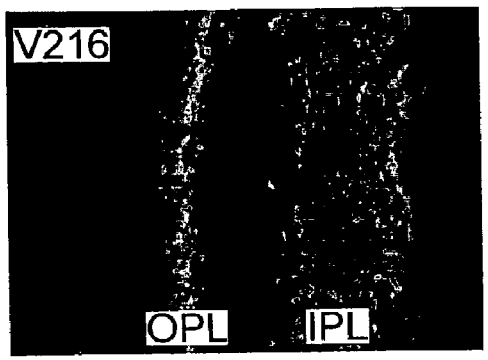
Figure 7T:
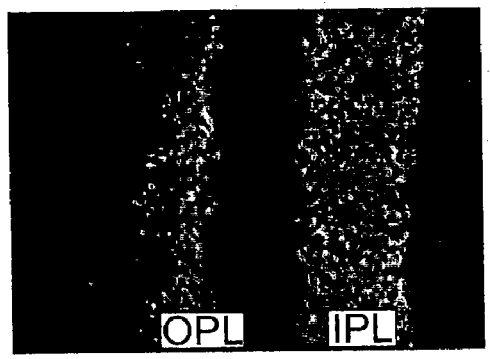
Figure 7U:
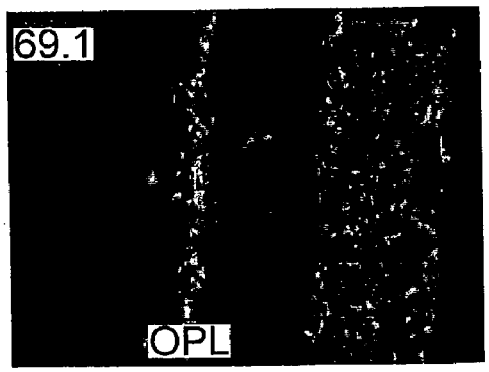
Figure 7V:
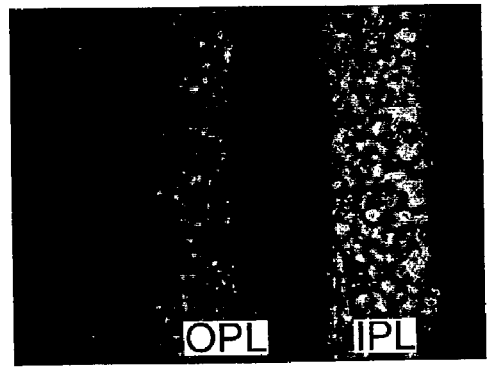
Figure 8A:
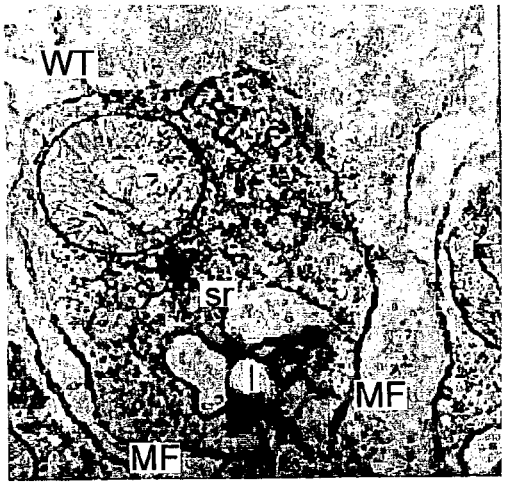
FIGS. 8A-D shows low-power electron micrographs of ribbon synapses from the retinae of wild-type (WT; A-C) and CSP knockout mice (KO; D). Degeneration of the synaptic terminals in the CSP KO mice is evident from the freely floating synaptic ribbons (SR) and loss of synaptic vesicles.
Figure 8B:
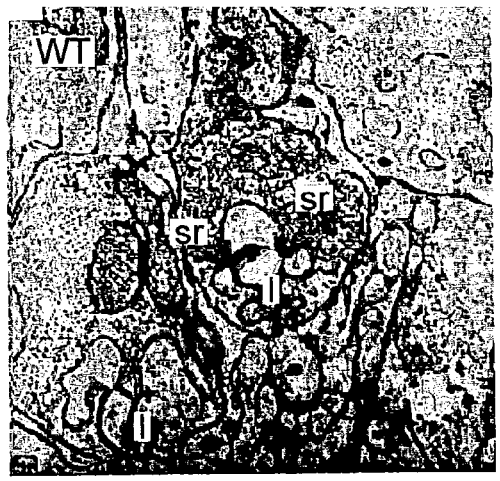
Figure 8C:
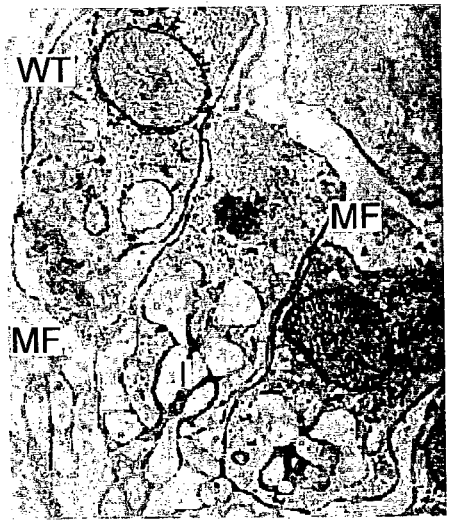
Figure 8D:
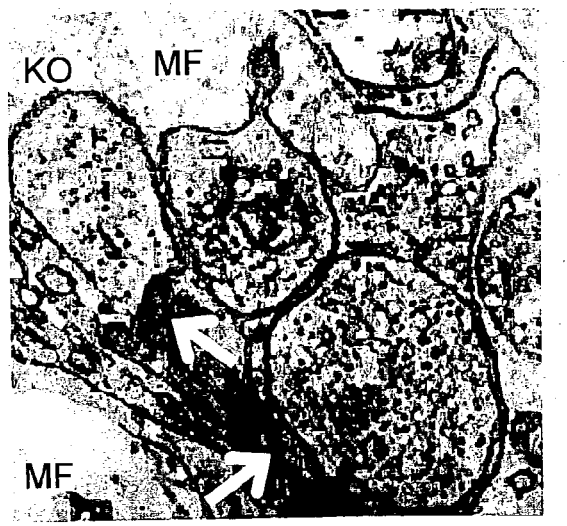

Immunohistochemical studies confirm the near-total depletion of CSP in the brains of the homozygous CSP KO mice (FIG. 5, compare A and B). However, synaptic function appears to be largely intact in these animals, as indicated by the robust immunohistochemical staining for the synaptic vesicle protein synaptoporin (FIG. 5C) and from the electrophysiological studies of synaptic charge (FIG. 6A, D, and G), vesicular pool size (FIG. 6B, E, and H) and vesicular release probability (FIG. 6C, F, and I), which show no significant decreases in these parameters. In these latter studies, hippocampal neurons from newborn mice were cultured and used for electrophysiological studies as previously described (Fernandez-Chacon et al., 2001, Nature 410:41-49). Briefly, neurons were cultured on microislands of glia cells so that neurons are isolated and form autapses. Whole-cell recordings from these neurons were performed using stimulation with action potentials and with hypertonic sucrose to determine the size of the evoked excitatory postsynaptic current (EPSC) and of the readily releasable pool, respectively. The ratio between these two measurements provides the vesicular release probability.

Although synaptic function seems relatively unimpaired, several pieces of evidence implicate CSP in the maintenance of synaptic function over the long term. First, homozygous CSP KO mice develop an ascending form of paralysis, which appears to play a significant role in the premature death of these animals. Furthermore, detailed observation of the retinae and neuromuscular junctions of homozygous CSP KO mice reveals major degenerative changes (FIGS. 7-9).

In these studies, young adult wild-type and CSP knockout mice were anesthetized and fixed by transcardial perfusion of paraformaldehyde. The retinae from the mice were sectioned on a cryostat, and analyzed by immunofluorescence staining using standard procedures as described elsewhere (von Kriegstein et al., 1998, *Eur. J. Neurosci.* 11:1335-1348; Schmitz et al, 2000, *Neuron* 28:857-872). The antibodies used were described above, and are indicated on the left upper corner of each picture (FIG. 7). The locations of the outer plexiform layer (OPL) corresponding to the photoreceptor synapses, and the inner plexiform layer (IPL) corresponding to the wider layer of synapses formed between bipolar, amacrine, and ganglion cell neurons, are indicated. Stained sections were examined in a confocal microscope.

For the electron microscopic slides shown in FIG. 8 and FIG. 9, young adult wild-type and knockout mice were anesthetized and fixed by transcardial perfusion with a glutaraldehyde/paraformaldehyde solution. The retinae from the mice were excised, sectioned, stained, and then thin-sectioned using standard procedures as described (Schoch et al., 2002, *Nature* 415:321-326). Sections were analyzed in an electron microscope. Degeneration of the synaptic terminals in the CSP KO mice is evident from the freely floating synaptic ribbons (SR) and loss of synaptic vesicles. Based on the findings of these studies, and those described above, CSP is required for optimal synaptic function.

Because they exhibit such a pronounced neurodegenerative phenotype, the CSP KO animals described above are clearly useful for elucidating the pathophysiology of various neurodegenerative diseases. Such animals will also be useful to identify agents that ameliorate or potentiate neurodegenerative disorders. The CSP KO animals may also be crossed to a wide variety of genetic models for neurodegenerative diseases, for example transgenic animals overexpressing mutant forms of synuclein as models of Parkinson's disease, or overexpressing wild-type or mutant forms of APP as models of Alzheimer's disease. Other transgenic animal models that may be crossed with the CSP KO mice include those for Alper's disease, amyotrophic lateral sclerosis, Huntington's disease, Lewy Body diseases, motor neuron diseases, multiple system atrophy, olivopontocerebellar atrophy, Pick's disease and related frontotemporal dementias, progressive supranuclear palsy, retinal degenerations including various forms of macular degeneration, tauopathies, and transmissible spongiform encephalopathies, where such models exist. The resulting doubly transgenic animals should display synergism that will enhance the neurodegenerative phenotypes of these animal models, allowing for more sensitive assays for the identification of possible therapeutic or diagnostic agents.

Example 5

Figure 10A:
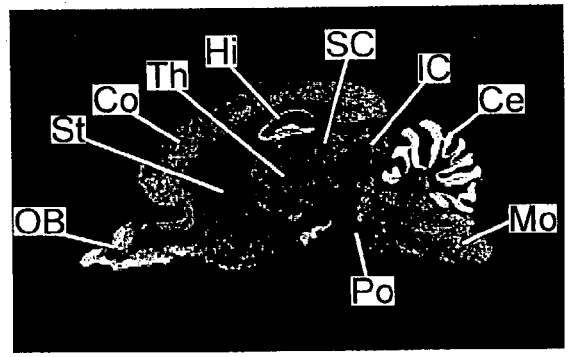
FIGS. 10A-C shows that the mRNAs of CSP (A), SGT (B), and Hsc70 (C) co-localize in rat whole-brain sections. Abbreviations: Ce, cerebellum; Co, cortex; Hi, hippocampus; IC, inferior colliculus; Mo, medulla oblongata; OB, olfactory bulb; Po, pons; SC, superior colliculus; St, striatum; Th, thalamus. Scale bar, 1 cm.
Figure 10B:
Figure 10C:

CSP, Hsc70, and SGT Form a Trimeric Complex on the Synaptic Vesicle Surface. As a first step to characterizing the localization of CSP, Hsc70, and SGT, the mRNA distribution of CSP, Hsc70, and SGT in adult rat brain was analyzed by applying an in situ hybridization technique (FIGS. 10A-C). Negative X-ray film images are shown. Two different oligonucleotides for each mRNA sequence were used; they exhibited essentially the same labeling pattern for the respective mRNAs. Controls with excess unlabeled oligonucleotides were devoid of signal (results not shown).

Detailed analyses of expression patterns of CSP, Hsc70, and SGT were performed with one oligonucleotide for each mRNA. Autoradiographs of hybridized rat brain sections revealed a high degree of overlap in the expression of the CSP, Hsc70, and SGT mRNAs (FIG. 10). These mRNAs are expressed throughout the brain, with highest levels in the cerebellum and the hippocampus. Strong labeling is observed in the CA regions and the dentate gyrus. Lower levels of mRNA expression are found in the cortex, olfactory bulb, thalamus, and striatum. In sum, the mRNA expression patterns for CSP, Hsc70, and SGT are consistent with a co-localization of the corresponding proteins in various brain regions.

Figure 11A:
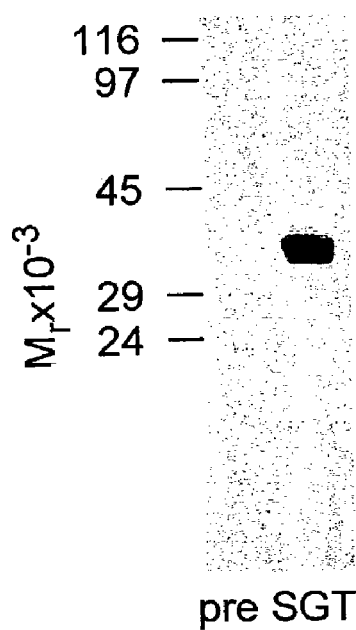
FIGS. 11A-E shows that CSP, SGT, and Hsc70 form a trimeric complex on synaptic vesicles. A. A polyclonal rabbit antibody raised against recombinant SGT specifically recognized a protein with a molecular weight of 35 kDa. B. Equal amounts of subcellular fractions from rat brain (20 µg/lane) were analyzed with specific antibodies. C. SGT was immunoprecipitated from isolated synaptic vesicles using a polyclonal mouse antibody, and the immunoprecipitates were analyzed with rabbit antibodies directed against diverse synaptic vesicle proteins. SGT, Hsc70, and CSP co-immunoprecipitated, demonstrating an interaction of these proteins on synaptic vesicles. Other synaptic vesicle proteins, such as rab3A, rabphilin, syntaxin, and SNAP25, lack in these immunoprecipitates and, therefore, are marked by asterisks. D. Synaptic vesicles were prepared from CSP knockout and wild-type mice. In a synaptic vesicle fraction from CSP knockout mice, SGT was drastically reduced compared with wild-type mice. Other synaptic proteins were unchanged. E. A quantitative analysis of synaptic vesicle proteins revealed a reduction of SGT by 72% in CSP knockout mice.

To assemble to a trimeric complex, it is a prerequisite that all three proteins are located in the same cellular compartment. In brain, CSP is primarily located on synaptic vesicles (Mastrogiacomo et al., 1994, *Science* 263:981-982). Hsc70, a cytosolic protein, is enriched in the nerve terminal (Ungewickell et al., 1995, *Nature* 378:632-635). To determine the localization of SGT, a polyclonal antibody was raised against recombinant SGT. As shown in FIG. 11A, the antibody was specific for SGT, a protein with a molecular weight of 35 kDa. This molecular weight agrees well with the expected value based on the amino acid composition of SGT.

Figure 11B:
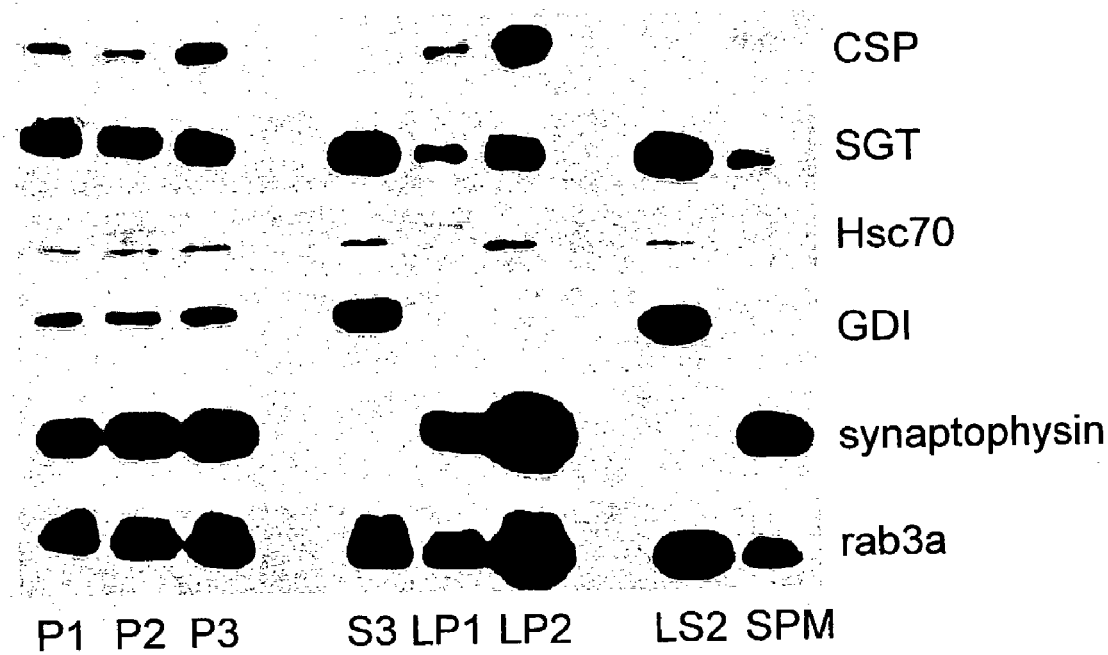

Since the antibody against SGT did not give a specific signal in immunocytochemistry, subcellular fractionations were performed. Antibodies directed against CSP, SGT, Hsc70, GDI, synaptophysin, and rab3a were used to characterize these fractions. In FIG. 11B, the subcellular fractions are designated as follows: P1, crude pellet with nuclei; P2, crude synaptosomal pellet; P3, light membrane pellet; S3, cytosolic fraction; LP1, lysed synaptosomal membranes; LP2, crude synaptic vesicle fraction; LS2, cytosolic synaptosomal fraction; SPM, synaptic plasma membranes.

CSP was mainly found in the synaptic vesicle fraction (LP2). It was not detectable in cytosolic fractions (S3, LS2), implying that the entire pool of CSP is subject to palmitoylation and membrane bound. SGT was predominantly found in cytosolic fractions (S3, LS2), consistent with a hydrophilic structure predicted from its amino acid sequence. However, significant amounts of SGT and Hsc70 were found in the synaptic vesicle fraction (LP2), strongly suggesting that SGT, Hsc70, and CSP co-localize on synaptic vesicles.

Synaptophysin, a synaptic vesicle marker (Jahn et al., 1985, *Proc. Natl. Acad. Sci. USA* 82:4137-4141), was highly enriched in LP2 and not detectable in cytosolic fractions, rab3A, a small G protein of the ras superfamily, was located on synaptic vesicles (LP2) and, as expected, found in soluble fractions (S3, LS2). GDI (Sasaki et al., 1990, *J. Biol. Chem.* 265:2333-2337) is a cytosolic protein that was not found in membrane fractions (LP1, LP2). Therefore, the possibility that LP2 was contaminated with LS2 could be excluded, supporting the idea that SGT and Hsc70 are recruited to vesicles by a resident synaptic vesicle protein.

Figure 11C:
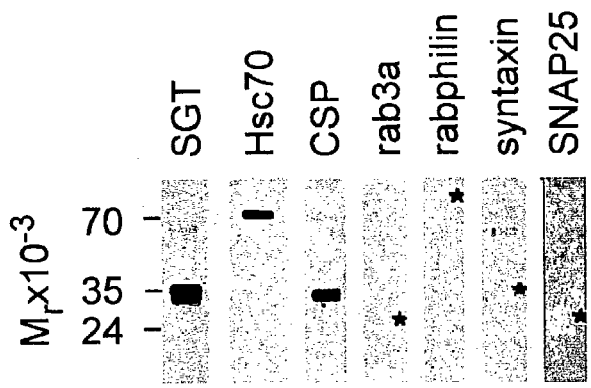
Figure 11D:
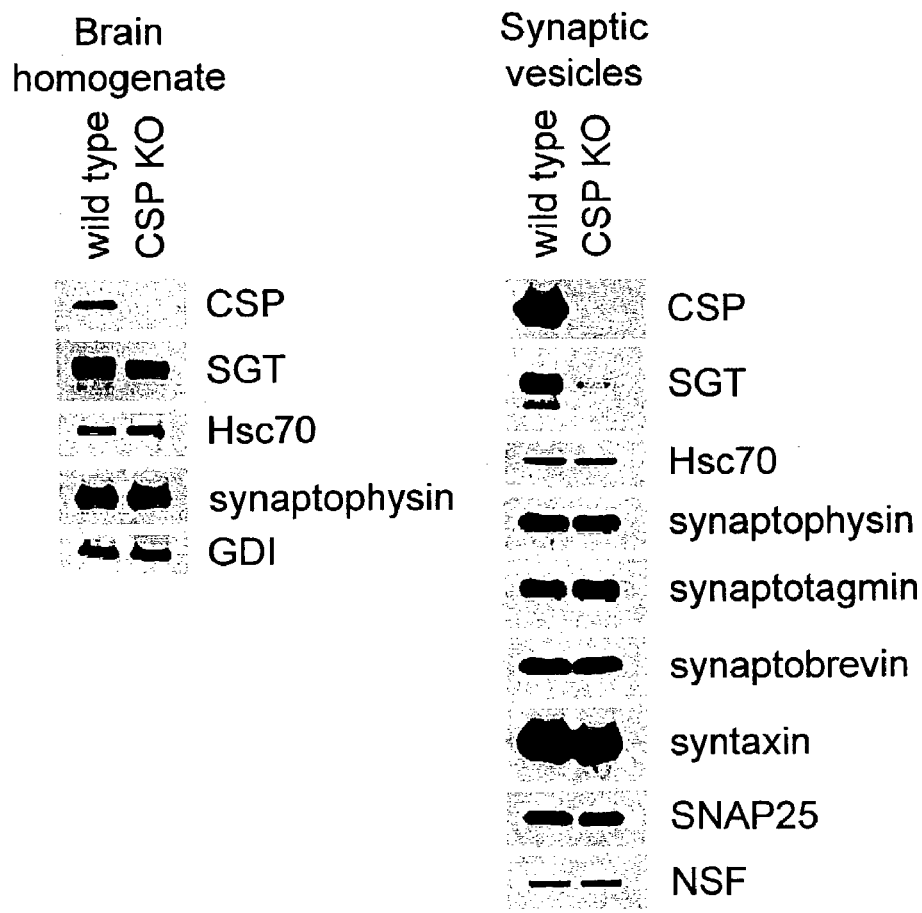

To examine whether CSP, Hsc70, and SGT form a trimeric complex on synaptic vesicles, SGT was immunoprecipitated from purified synaptic vesicles using a polyclonal mouse antibody raised against SGT (FIG. 11C). In the resulting immunoprecipitate, Hsc70 and CSP but not rab3a, rabphilin, syntaxin, and SNAP25 could be detected. These results demonstrate that SGT, Hsc70, and CSP specifically co-immunoprecipitate from purified synaptic vesicles without contamination of other synaptic vesicle proteins.

Figure 11E:
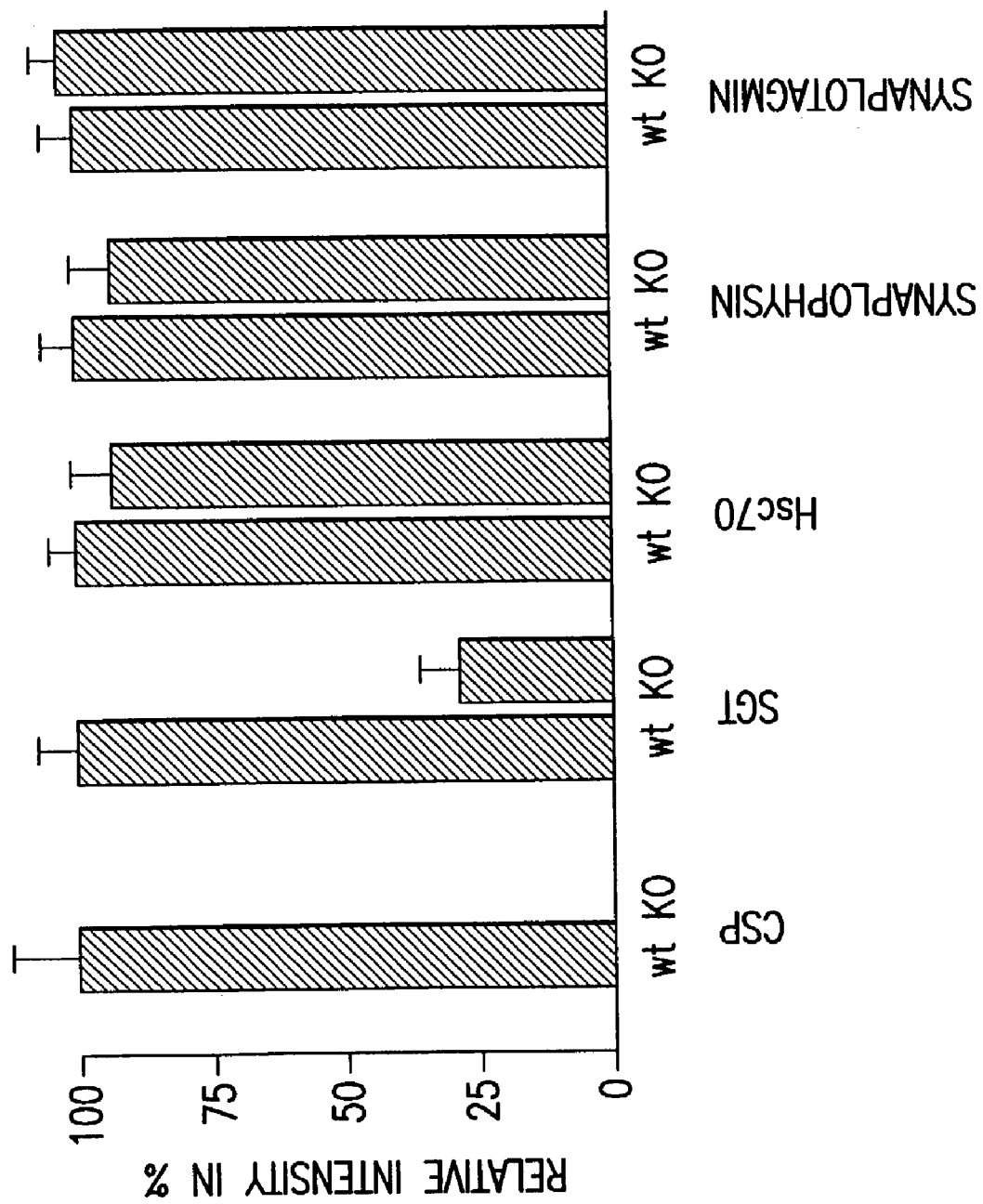

To test if the interaction of CSP with SGT is biologically important in vivo, a CSP knockout mouse was used. CSP knockout mice are viable until 4-5 weeks after birth, making it possible to study them biochemically. In total brain homogenates, no significant changes in SGT and Hsc70 levels were detected compared to wild-type controls (FIG. 1D). However, when synaptic vesicles purified from CSP knockout mice were examined, a selective decrease of SGT on synaptic vesicles was observed. Quantitations revealed that SGT was decreased more than 70% on the vesicles, while the levels of other proteins were unaffected (FIG. 11E). These data suggest that CSP biologically interacts with SGT in vivo and is required for the recruitment of SGT to synaptic vesicles.

Example 6

Figure 12A:
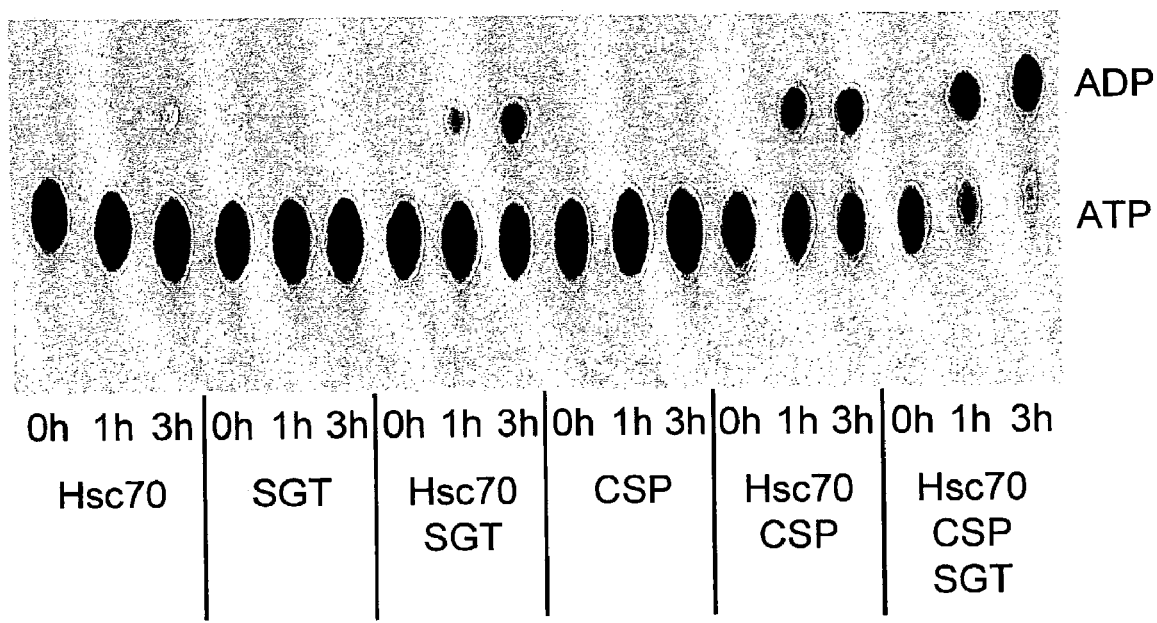
FIGS. 12A-C shows that, as components of a trimeric chaperone complex, SGT and CSP strongly activate the Hsc70 ATPase. A. ATPase activities of various combinations of rat CSP, SGT, and Hsc70. At the indicated times, hydrolysis of [α-32P] ATP was determined by thin layer chromatography and autoradiography. B. A quantification of these data with the aid of a PhosphorImager revealed a first-order kinetics for short incubation times (within 1 hr). A combination of all three proteins induced a strong activation of the Hsc70 ATPase (19-fold). C. Chaperone activities of CSP, SGT and Hsc70.

SGT and CSP Activate the ATPase of Hsc70. As already reported (Braun et al., 1996, *Neuropharmacology* 34:1361-1369; Chamberlain and Burgoyne, 1997, *Biochem. J.* 322: 853-858), CSP strongly activated the Hsc70 ATPase with stimulation factor of ~12. Thus, the ability of SGT to affect the ATPase activity of Hsc70 was next examined. In these studies, [$\alpha$-$^{32}$P] ATP was incubated with various combinations of bacterially expressed rat CSP, SGT, and Hsc70 in stoichiometric ratios of 1:1:1. At the indicated times, hydrolysis of [$\alpha$-$^{32}$p] ATP was determined by thin layer chromatography and autoradiography. SGT alone did not induce ATP hydrolysis (FIG. 12A). Hsc70 exhibited a weak intrinsic ATPase activity. This ATPase activity was significantly increased by SGT, demonstrating a functional interaction between SGT and Hsc70 (FIG. 12A). Compared to the ATPase activation by CSP (~12-fold), the stimulation by SGT was weaker (~3-fold). A combination of CSP and SGT resulted in a dramatic ATPase activation (~19-fold) (FIG. 5A). Since all three components are present in equimolar amounts, the effects of CSP and SGT on the Hsc70 ATPase activity are superadditive. Interestingly, the ATPase activation by CSP could not be increased by higher concentrations of CSP (data not shown), implying that CSP and SGT bind to distinct domains in Hsc70. This conclusion is indeed confirmed by mapping the respective binding domains (see FIG. 1C).

Figure 12B:
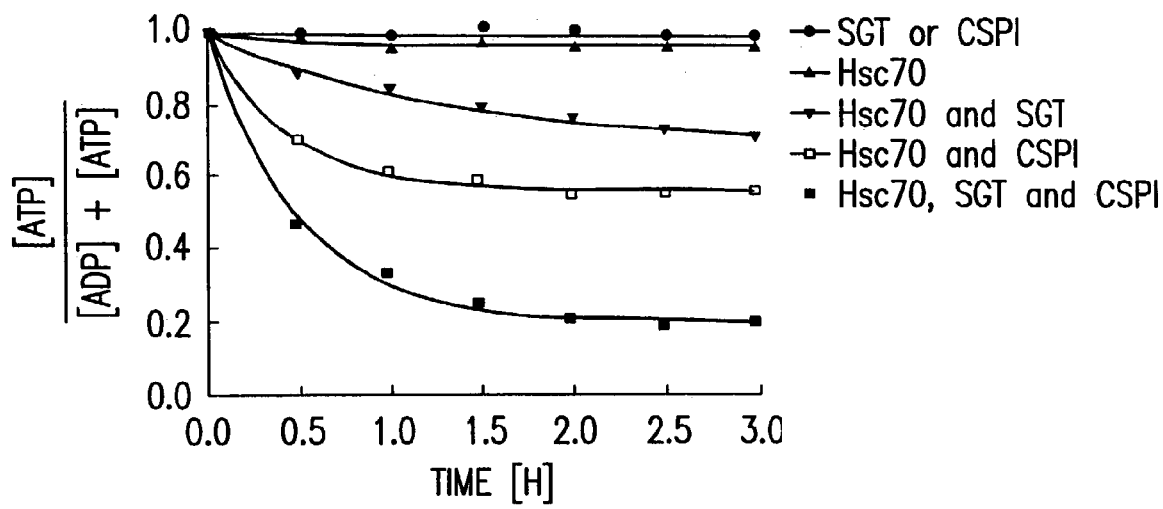

A quantitative analysis of the hydrolysis kinetics provided initial rate constants as follows (given in nmol×l$^{-1}$×h$^{-1}$): $v_0$(Hsc70)=0.42; $v_0$(Hsc70 and SGT)=1.22; $v_0$(Hsc70 and CSP)=4.95; $v_0$(Hsc70, SGT, and CSP)=7.91 (FIG. 12B). Note that equimolar amounts of all three proteins were used to determine these rate constants. An exponential fit of the ATP hydrolysis data revealed a first-order kinetics during the first hour of incubation. Thereafter, a significant deviation from first-order kinetics was observed, suggesting that a partial inactivation of Hsc70 occurred during prolonged incubation times.

Example 7

The Trimeric Complex Consisting of CSP, SGT, and Hsc70 Has Chaperone Activity. Three reasons prompted a study of the potential chaperone activity of the trimeric complex composed of CSP, SGT, and Hsc70. First, as typical for chaperones, the CSP/Hsc70/SGT complex undergoes an association-dissociation cycle as a function of ADP and ATP, respectively. Second, CSP and SGT combined strongly activate the Hsc70 ATPase, most likely providing the free energy for refolding of a misfolded protein. Third, Hsc70 in combination with certain co-chaperones is known to act as chaperone (Hohfeld et al., 1995, *Cell* 83:589-598).

To address the possibility that our trimeric complex behaves as a chaperone, denatured firefly luciferase was used as an artificial substrate. This assay is well established to study chaperone activities of proteins and protein complexes because the enzymatic activity of luciferase can easily be determined by measurement of bioluminescence (Szabo et al., 1994, *Proc. Natl. Acad. Sci. USA* 91:10345-10349). Briefly, denatured firefly luciferase was diluted 100-fold into a buffer containing various combinations of CSP, SGT, and Hsc70 in the presence of either ATP or ADP. Luciferase activities were determined after 1 hr incubation at 30° C. Activities are expressed as percentage of native luciferase activity.

Figure 12C:
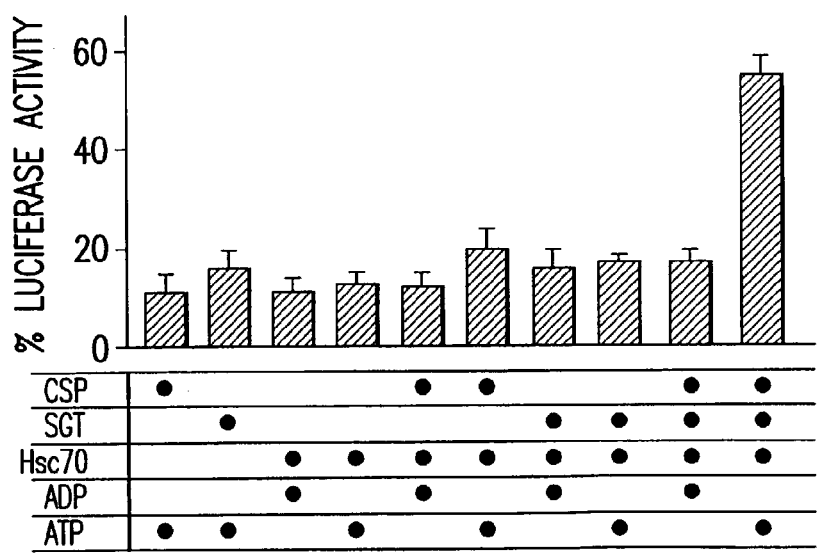

In these studies, SGT seems to have a weak and ATP-independent chaperone activity (FIG. 12C, column 2). Hsc70 alone did not mediate the refolding of luciferase (FIG. 12C, column 3 and 4). A combination of CSP and Hsc70 achieved a weak chaperone activity as a function of ATP (FIG. 12C, columns 5 and 6). However, when unfolded luciferase was incubated with a mixture of CSP, SGT, and Hsc70, renaturation of ~60% of the enzyme was observed (FIG. 12C, column 10). Efficient renaturation required all three proteins, and was dependent on the presence of ATP (compare FIG. 12C, columns 9 and 10). These studies suggest that SGT increases the efficiency of the CSP/Hsc70 system in this refolding reaction through both its ability to stabilize the CSP/Hsc70 complex and to activate the ATPase of Hsc70.

Example 8

Figure 13A:
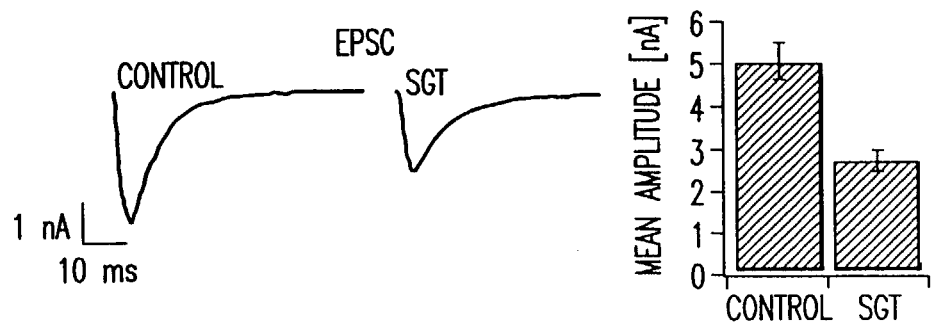
FIGS. 13A-C shows that overexpression of SGT in hippocampal neurons leads to a reduction in synaptic transmission. SGT/GFP was transiently overexpressed in hippocampal neurons. A. Neurons were stimulated at a frequency of 0.2 Hz and the resulting excitatory postsynaptic currents (EPSC) were recorded. B. Determination of the readily releasable vesicle pool size by application of hypertonic sucrose solution. C. Synaptic depression rate in neurons transfected with SGT/GFP.

SGT Overexpression in Intact Synapses Leads to a Reduction of Synaptic Transmission. The physiological consequences of the CSP/Hsc70/SGT interaction on synaptic transmission at intact synapses was next examined. For this purpose, a fusion protein consisting of SGT and green fluorescent protein (GFP) was transiently overexpressed in hippocampal neurons grown in microisland culture (Bekkers and Stevens, 1991, *Proc. Natl. Acad. Sci. USA* 88:7834-7838). Six to eighteen hours after infection, isolated neurons were stimulated at a frequency of 0.2 Hz and the resulting autaptic postsynaptic currents were measured. As shown in FIG. 13A, overexpression of SGT resulted in a marked and statistically highly significant reduction in EPSC amplitude to about 53% of the amplitude of control cells (2.66±0.25 nA, n=58 for SGT-overexpressing cells versus 5.00±0.44 nA, n=66 for control cells; p<0.0001). Since it has been previously that neurons infected with green fluorescent protein alone display no reduction in mean amplitude (Lao et al., 2000, *Neuron* 25:191-201), the reduction in EPSC is most likely a specific effect of the overexpression of SGT.

Figure 13B:
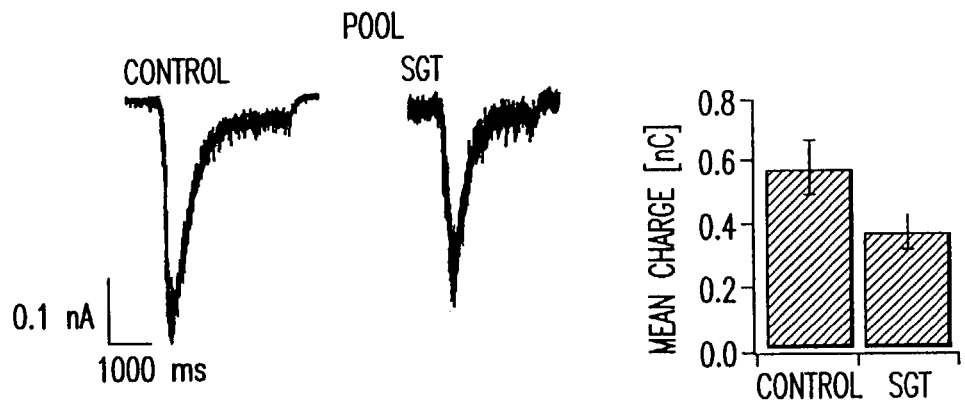

To determine if the observed reduction of EPSCs in SGT-overexpressing neurons is due to an underlying reduction in the size of the readily releasable vesicle pool, the size of this pool was assayed by application of hypertonic sucrose solution. These studies demonstrated that excitatory postsynaptic responses induced by application of hypertonic sucrose solution were reduced by approximately 30% in neurons overexpressing SGT relative to control neurons (FIG. 13B, left). However, the degree of this reduction was less than that observed for synaptically evoked responses (total charge transfer 0.58±0.086 nC, n=33, in control cells; 0.38±0.052 nC, n=32, in SGT-overexpressing cells, p<0.05; FIG. 13B, right). Consequently, the ratio between total charge transfer during an EPSC and that during sucrose stimulation was also altered when SGT-overexpressing cells were compared to wild-type control cells (0.088±0.006, n=33, in control cells; 0.060±0.006, n=32, in SGT-overexpressing cells, p<0.002). These data suggest that SGT overexpression leads, in addition to a reduction in pool size, also to a reduction in vesicular release probability.

Figure 13C:
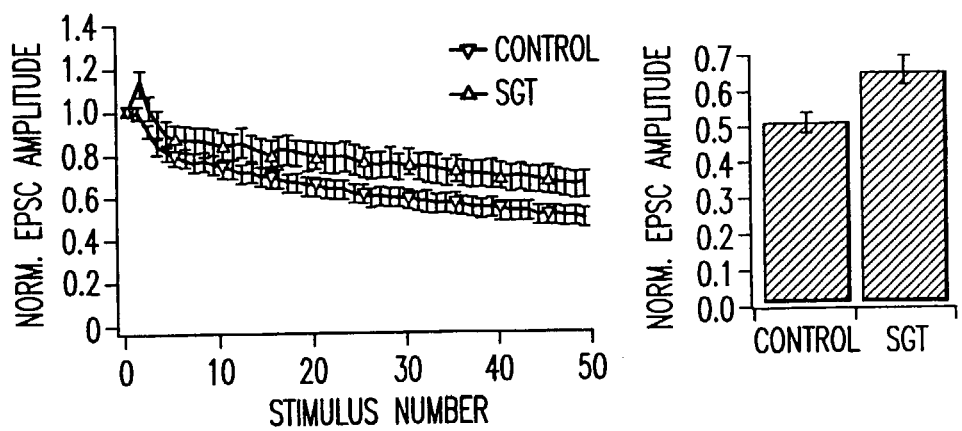

To further confirm this possibility, cells were stimulated with 50 stimuli at 10 Hz. Since autaptic responses in cultured hippocampal neurons are characterized by a marked activity-dependent depression (Mennerick and Zorumski, 1995, *J. Physiol.* 488:85-101; Rosenmund and Stevens, 1996, *Neuron* 16:1197-1207), a reduction in release probability should be reflected in a less pronounced depression. Indeed, SGT-overexpressing cells displayed an average steady-state depression level of 65.3±6.1% (n=22), which is significantly higher (p<0.05) than that from control cells, which had an average steady-state depression level of 50.0±4.8% (FIG. 13C). From these studies, it appears that the observed decrease in synaptic transmission upon overexpression of SGT is caused by both a reduction in the size of the readily releasable pool and a reduction in vesicular release probability.

Example 9

Figure 14:
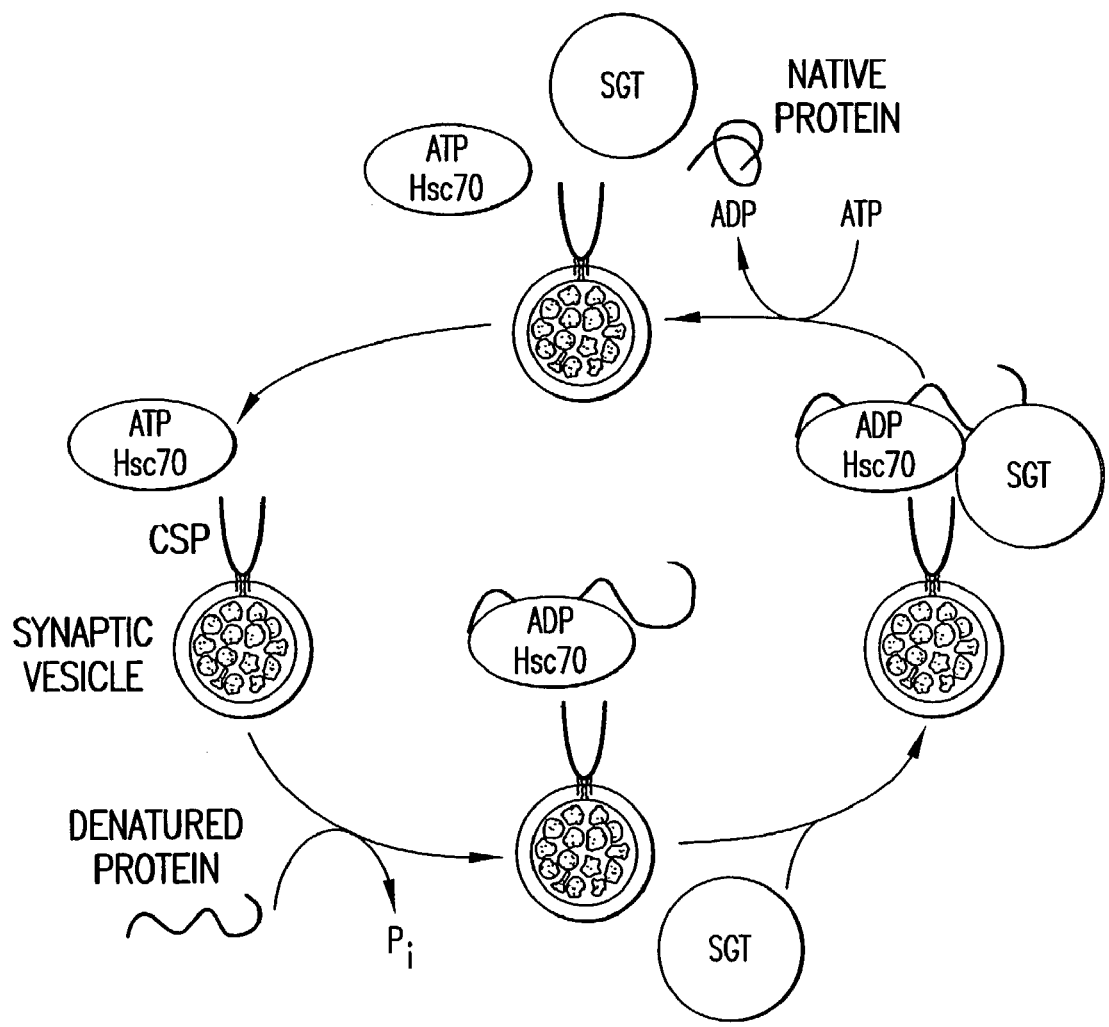
FIG. 14 shows a model of the association-dissociation cycle of the CSP/Hsc70/SGT complex on the synaptic vesicle surface.

Model of the association-dissociation cycle of the CSP/Hsc70/SGT complex on the synaptic vesicle surface. Based on the foregoing evidence, the working model shown in FIG. 14 has been proposed for the function of the tripartite CSP/Hsc70/SGT complex on the synaptic vesicle surface. According to this model, the J domain of CSP recruits Hsc70 to the synaptic vesicle surface. The C-terminal domain of CSP binds to SGT, thereby forming a trimeric protein complex. This complex is stabilized by interactions between Hsc70 and SGT. The findings from the Examples described above suggest that the tripartite complex has a chaperone activity for a misfolded protein or for a protein complex that does not spontaneously dissociate. In vertebrates, direct and indirect interactions of CSP with voltage-gated $Ca^{2+}$-channels have been demonstrated (Leveque et al., 1998, *J. Biol. Chem.* 273: 13488-13492; Magga et al., 2000, *Neuron* 28:195-204). CSP has also been proposed to bind to the SNAREs syntaxin (Nie et al., 1999, *J. Neurosci.* 19:10270-10279) or synaptobrevin/VAMP (Leveque et al., 1998, *J. Biol. Chem.* 273:13488-13492). These findings suggest that the CSP/Hsc70/SGT complex may restore the biological activity of voltage-gated $Ca^{2+}$ channels either by transferring them into a SNARE complex, or rescuing them from such a complex.

Example 10

Generation and Characterization of Transgenic Mice Overexpressing CSP and SGT and/or Hsc70. Transgenic animals overexpressing CSP, either alone or in combination with the overexpression of SGT and Hsc70, are also very useful in understanding the pathophysiology of neurodegenerative diseases and for identifying environmental or other agents that contribute to the development and progression of these diseases.

These animals may be created using various techniques well known to those skilled in the art. Specifically, DNA fragments containing a selectable marker and one or more expression cassettes comprised of the open reading frame for CSP or SGT or Hsc70 flanked by a promoter and a polyadenylation signal can be injected into embryonic stem cells. The DNA fragment to be inserted may introduce one or more copies of an expression cassette encoding biologically active CSP, SGT or Hsc70 into the genome of the transgenic animal, and may be introduced at a single site or at multiple sites within the genome of the host. Promoters to be incorporated into the expression cassette include those that produce constitutive, high level expression, such as the CMV, EF-1α or SRα promoters, those that produce region-neuron-specific expression, such as the CaM kinase II or rhodopsin promoters, or those that permit regulatable expression, such as the tet on or tet off promoters or the steroid-inducible GeneSwitch™ system.

The embryonic stem cells in which the DNA fragment has stably integrated may be identified by means of the selectable marker present in the DNA fragment. These cells can then be transferred into blastocysts; which can be implanted into the reproductive tract of a pseudopregnant female recipient. The offspring resulting from this procedure can be screened by Southern analysis or polymerase chain reaction (PCR) for the presence of the transgenic sequences. Individuals containing the transgene can be crossed to obtain individuals that are heterozygous and homozygous for the transgene. This procedure may be used to produce animals overexpressing CSP alone or overexpressing CSP and SGT and/or Hsc70. While these animals may lack a pronounced phenotype in the absence of any external or internal intervention, such animals should display enhanced resistance to chemical, environmental or genetic agents that induce neurodegeneration. Thus, such animals will be useful for identifying agents that contribute to the development or progression of neurodegenerative diseases or that are useful for the treatment and/or prevention of these diseases.

All references cited herein are incorporated herein in their entirety.

REFERENCES

Augustin I., Betz A., Herrmann C., Jo T. and Brose N. (1999) Differential expression of two novel Munc13 proteins in rat brain. *Biochem. J.* 337:363-371.

Auluck; P. K. Chan, H. Y., Trojanowski, J. Q., Lee, V. M., and Bonini, N. M. (2002). Chaperone suppression of alpha-synuclein toxicity in a *Drosophila* model for Parkinson's disease. *Science* 295(5556):865-868.

Bekkers J. M. and Stevens C.F. (1991) Excitatory and inhibitory autaptic currents in isolated hippocampal neurons maintained in culture. *Proc. Natl. Acad. Sci. USA* 88:7834-7838.

Blatch G. L. and Lässle M. (1999) The tetratricopeptide repeat: a structural motif mediating protein-protein interactions. *Bioessays* 21:932-939.

Braun J. E. and Scheller R. H. (1995) Cysteine string protein, a DnaJ family member, is present on diverse secretory vesicles. *Neuropharmacology* 34:1361-1369.

Braun J. E. A., Wilbanks S. M. and Scheller R. H. (1996) The cysteine string secretory vesicle protein activates Hsc70 ATPase. *J. Biol. Chem.* 271:25989-25993.

Bronk B., Wenniger J. J., Dawson-Scully K., Guo X., Hong S., Atwood H. L. and Zinsmaier K. E. (2001) *Drosophila* Hsc70-4 is critical for neurotransmitter exocytosis in vivo. *Neuron* 30:475-488.

Buchner E. and Gundersen C. B. (1997) The DnaJ-like cysteine string protein and exocytotic neurotransmitter release. *Trends Neurosci.* 20:223-227.

Callahan M. A., Handley M. A., Lee Y. H., Talbot K. J., Harper J. W. and Panganiban A. T. (1998) Functional interaction of human immunodeficiency virus type 1 Vpu and Gag with a novel member of the tetratricopeptide repeat protein family. *J. Virol.* 72:5189-5197.

Chamberlain L. H. and Burgoyne R. D. (1997) Activation of the ATPase activity of heat-shock proteins Hsc70/Hsp70 by cysteine-string protein. *Biochem. J.* 322:853-858.

Chamberlain L. H. and Burgoyne R. D. (1998) The cysteine-string domain of the secretory vesicle cysteine-string protein is required for membrane targeting. *Biochem. J.,* 335:205-209.

Chamberlain L. H., Henry J. and Burgoyne R. D. (1996) Cysteine string proteins are associated with chromaffin granules. *J. Biol. Chem.* 271:19514-19517.

Cummings, C. J., Sun, U., Opal, P., Antalffy, B., Mestril, R., Orr, H. T., Dillmann, W. H., and Zoghbi, H. Y. (2001). Over-expression of inducible HSP70 chaperone suppresses neuropathology and improves motor function in SCA1 mice. *Hum. Mol. Genet.* 10:1511-1518.

Cziepluch C., Kordes E., Poirey R., Grewenig A., Rommelaere J. and Jauniaux J. C. (1998) Identification of a novel cellular TPR-containing protein, SGT, that interacts with the nonstructural protein NS1 of parvovirus H-1. *J. Virol.* 72:4149-4156.

Dawson-Scully K., Bronk P., Atwood H. L. and Zinsmaier K. E. (2000) Cysteine-string protein increases the calcium sensitivity of neurotransmitter exocytosis in *Drosophila J. Neurosci.* 20:6039-6047.

Fernandez-Chacon, R., Konigstorfer, A., Gerber, S. H., Garcia, J., Matos, M. F., Stevens, C. F., Brose, N., Rizo, J., Rosenmund, C., Südhof, T. C. (2001) Synaptotagmin I functions as a calcium regulator of release probability. *Nature* 410:41-9.

Fernandez-Funez, P., Nino-Rosales, M. L., de Gouyon, B., She, W. C., Luchak, J. M., Martinez, P., Turiegano, E. Benito, J., Capovilla, M., Skinner, P. J., McCall, A., Canal, I., Orr, H. T., Zoghbi, H. Y., Botas, J. (2000). Identification of genes that modify ataxin-1-induced neurodegeneration. *Nature* 408:101-106.

Fink A. L. (1999) Chaperone-mediated protein folding. *Physiol. Rev.* 79:425-449.

Goedert, M. (2001). Alpha-synuclein and neurodegenerative diseases. *Nat. Rev. Neurosci.* 2:492-501.

Graham M. E. and Burgoyne R. D. (2000) Comparison of cysteine string protein (Csp) and mutant alpha-SNAP overexpression reveals a role for csp in late steps of membrane fusion in dense-core granule exocytosis in adrenal chromaffin cells. *J. Neurosci,* 20:1281-1289.

Guan K. L. and Dixon J. E. (1991) Eukaryotic proteins expressed in *Escherichia coli*: an improved thrombin cleavage and purification procedure of fusion proteins with glutathione S-transferase. *Anal. Biochem.* 192:262-267.

Gundersen C. B. and Umbach J. A. (1992) Suppression cloning of the cDNA for a candidate subunit of a presynaptic calcium channel. *Neuron* 9:527-537.

Gundersen C. B., Mastrogiacomo A., Faull K. and Umbach J. A. (1994) Extensive lipidation of a Torpedo cysteine string protein. *J. Biol. Chem.* 269:19197-19199.

Hartl, F. U., and Hayer-Hartl, M. (2002). Molecular chaperones in the cytosol: from nascent chain to folded protein. *Science* 295:1852-1858.

Hendrick J. P. and Hartl F. U. (1995) The role of molecular chaperones in protein folding. *Faseb J,* 9:1559-1569.

Hohfeld J., Minami Y. and Hartl F. U. (1995) Hip, a novel cochaperone involved in the eukaryotic Hsc70/Hsp40 reaction cycle. *Cell* 83:589-598.

Jahn R., Schiebler W., Ouimet C. and Greengard P. (1985) A 38,000-dalton membrane protein (p38) present in synaptic vesicles. *Proc. Natl. Acad. Sci. USA* 82:4137-4141.

Kazemi-Esfarjani, P., and Benzer, S. (2000). Genetic suppression of polyglutamine toxicity in *Drosophila*. *Science* 287:1837-1840.

Laemmli U. K. (1970) Cleavage of structural proteins during the assembly of the head of bacteriophage T4. *Nature* 227:680-685.

Lao G., Scheuss V., Gerwin C. M., Su Q., Mochida S., Rettig J. and Sheng Z. H. (2000) Syntaphilin: a syntaxin-1 clamp that controls SNARE assembly. *Neuron* 25:191-201.

Leveque C., Pupier S., Marqueze B., Geslin L., Kataoka M., Takahashi M., De W. M. and Seagar M. (1998) Interaction of cysteine string proteins with the alpha1A subunit of the P/Q-type calcium channel. *J. Biol. Chem.* 273:13488-13492.

Liu F. H., Wu S. J., Hu S. M., Hsiao C. D. and Wang C. (1999) Specific interaction of the 70-kDa heat shock cognate protein with the tetratricopeptide repeats. *J. Biol. Chem.* 274: 34425-34432.

Magga J. M., Jarvis S. E., Arnot M. I., Zamponi G. W. and Braun J. E. (2000) Cysteine string protein regulates G protein modulation of N-type calcium channels. *Neuron* 28:195-204.

Mastrogiacomo A., Parsons S. M., Zampighi G. A., Jenden D. J., Umbach J. A. and Gundersen C. B. (1994) Cysteine string proteins: a potential link between synaptic vesicles and presynaptic $Ca^{2+}$ channels. *Science* 263:981-982.

Mennerick S. and Zorumski C. F. (1995) Paired-pulse modulation of fast excitatory synaptic currents in microcultures of rat hippocampal neurons. *J. Physiol,* 488:85-101.

Nie Z., Ranjan R., Wenniger J. J., Hong S. N., Bronk P. and Zinsmaier K. E. (1999) Overexpression of cysteine-string proteins in *drosophila* reveals interactions with syntaxin. *J. Neurosci.* 19:10270-10279.

Noji H., Yasuda R., Yoshida M. and Kinosita K. Jr. (1997) Direct observation of the rotation of F1-ATPase. *Nature* 386: 299-302.

Ranjan R., Bronk P. and Zinsmaier K. E. (1998) Cysteine string protein is required for calcium secretion coupling of evoked neurotransmission in *drosophila* but not for vesicle recycling. *J. Neurosci.* 18:956-964.

Rosahl T. W., Geppert M., Spillane D., Herz J., Hammer R. E., Malenka R. C. and Südhof T. C. (1993) Short-term synaptic plasticity is altered in mice lacking synapsin I. *Cell* 75:661-670.

Rosenmund C. and Stevens C.F. (1996) Definition of the readily releasable pool of vesicles at hippocampal synapses. *Neuron* 16:1197-1207.

Sasaki T., Kikuchi A., Araki S., Hata Y., Isomura M., Kuroda S. and Takai Y. (1990) Purification and characterization from bovine brain cytosol of a protein that inhibits the dissociation of GDP from, and the subsequent binding of GTP to smg p25A, a ras p21-like GTP-binding protein. *J. Biol. Chem,* 265:2333-2337.

Scales S. J. and Scheller R. H. (1999) Lipid membranes shape up. *Nature* 401:123-124.

Schiestl R. H. and Gietz R. D. (1989) High efficiency transformation of intact yeast cells using single stranded nucleic acids as a carrier. *Curr. Genet,* 16:339-346.

Schoch, S., Castillo P. E., Jo T., Mukherjee K., Geppert M., Wang Y., Schmitz F., Malenka R. C. and Südhof, T. C. (2002) RIM1α forms a protein scaffold for regulating neurotransmitter release at the active zone. *Nature* 415:321-326.

Schmitz F., Konigstorfer A., and Südhof T. C. (2000) RIBEYE, a component of synaptic ribbons: A protein's journey through evolution provides insight into how synaptic ribbons function. *Neuron* 28:857-872.

Selkoe, D. J. (2001). Alzheimer's disease: genes, proteins, and therapy. *Physiol. Rev.* 81:741-766.

Sherman, M. Y., and Goldberg, A. L. (2001). Cellular defenses against unfolded proteins: a cell biologist thinks about neurodegenerative diseases. *Neuron* 29:15-32.

Smith D. B. and Johnson K. S. (1988) Single-step purification of polypeptides expressed in *Escherichia coli* as fusions with glutathione S-transferase. *Gene* 67:31-40.

Stahl B., Chou J. H., Li C., Südhof T. C. and Jahn R. (1996) Rab3 reversibly recruits rabphilin to synaptic vesicles by a mechanism analogous to raf recruitment by ras. *EMBO J.* 15:1799-1809.

Stahl B., Tobaben S. and Südhof T. C. (1999) Two distinct domains in hsc70 are essential for the interaction with the synaptic vesicle cysteine string protein. *Eur. J. Cell Biol.* 78:375-381.

Südhof T. C. (1995) The synaptic vesicle cycle: a cascade of protein-protein interactions. *Nature,* 375:645-653.

Südhof T. C. (2000) The synaptic vesicle cycle revisited. *Neuron* 28:317-320.

Szabo A., Langer T., Schroder H., Flanagan J., Bukau B. and Hartl F. U. (1994) The ATP hydrolysis-dependent reaction cycle of the *Escherichia coli* Hsp70 system DnaK, DnaJ, and GrpE. *Proc. Natl. Acad. Sci. USA* 91:10345-10349.

Tobaben, S., Thakur, P., Fernandez-Chacon, R., Südhof, T. C., Rettig, J., Stahl, B. (2001) A trimeric protein complex functions as a synaptic chaperone machine. *Neuron* 31:987-999.

Towbin H., Staehelin T. and Gordon J. (1979) Electrophoretic transfer of proteins from polyacrylamide gels to nitrocellulose sheets: procedure and some applications. *Proc. Natl. Acad. Sci. USA* 76:4350-4354.

Ungewickell E., Ungewickell H., Holstein S. E., Lindner R., Prasad K., Barouch W., Martin B., Greene L. E. and Eisenberg E. (1995) Role of auxilin in uncoating clathrin-coated vesicles. *Nature* 378:632-635.

Vojtek A. B., Hollenberg S. M. and Cooper J. A. (1993) Mammalian Ras interacts directly with the serine/threonine kinase Raf. *Cell* 74:205-214.

von Kriegstein K., Schmitz F., Link E. and Südhof T. C. (1998) Distribution of synaptic vesicle proteins in the mammalian retina identifies obligatory and facultative components of ribbon synapses. *Eur. J. Neurosci.* 11:1335-1348.

Walch-Solimena C., Blasi J., Edelmann L., Chapman E. R., von Mollard G. and Jahn R. (1995) The t-SNAREs syntaxin 1 and SNAP-25 are present on organelles that participate in synaptic vesicle recycling. *J. Cell Biol.* 128:637-645.

Warrick, J. M., Chan, H. Y., Gray-Board, G. L., Chai, U., Paulson, H. L. and Bonini, N. M. (1999). Suppression of polyglutamine-mediated neurodegeneration in *Drosophila* by the molecular chaperone HSP70. *Nat. Genet.* 23:425-428.

Wu M. N., Fergestad T., Lloyd T. E., He Y., Broadie K. and Bellen H. J. (1999) Syntaxin 1A interacts with multiple exocytic proteins to regulate neurotransmitter release in vivo. *Neuron* 23:593-605.

Young J. C., Obermann W. M. and Hartl F. U. (1998) Specific binding of tetratricopeptide repeat proteins to the C-terminal 12-kDa domain of hsp90. *J. Biol. Chem.* 273: 18007-18010.

Zinsmaier K. E., Hofbauer A., Heimbeck G., Pflugfelder G. O., Buchner S. and Buchner E. (1990) A cysteine-string protein is expressed in retina and brain of *Drosophila. J. Neurogenet.* 7:15-29.

Zinsmaier K. E., Eberle K. K., Buchner E., Walter N. and Benzer S. (1994) Paralysis and early death in cysteine string protein mutants of *Drosophila. Science* 263:977-980.

Zoghbi, H. Y., and Orr. H. T. (2000). Glutamine repeats and neurodegeneration. *Annu. Rev. Neurosci.* 23:217-247.

We claim:

1. A method for identifying agents useful for maintaining long-term synaptic function, comprising:
   (i) establishing a model of impaired synaptic function by:
      (a) contacting a cell expressing CSP, SGT and Hsc70 with a first agent;
      (b) measuring the levels of CSP chaperone activity obtained in the presence and absence of the first agent;
      (c) comparing the levels of CSP chaperone activity measured in step (b) wherein decreased levels of CSP chaperone activity in the presence of the agent indicate that the first agent contributes to the development or progression of neurodegenerative disorders; and
      (d) contacting a cell comprising CSP, SGT and Hsc70 with the first agent if the first agent contributes to the development or progression of neurodegenerative disorders;
   (ii) contacting the cell of step (d) with a second agent;
   (iii) measuring the levels of CSP chaperone activity obtained in the presence of the first agent and in the presence and absence of the second agent; and
   (iv) comparing the levels of CSP chaperone activity measured in step (iii) wherein increased levels of CSP chaperone activity in the presence of the second agent relative to the levels of CSP chaperone activity in the absence of the second agent indicate that the second agent is useful for maintaining long-term synaptic function.

2. A method for identifying candidate compounds for the treatment of Alzheimer's Disease, comprising:
   (a) providing a first cell and a second cell expressing APP, CSP, SGT, and Hsc70;
   (b) contacting the first cell with a test agent;
   (c) measuring the levels of CSP chaperone activity in the first cell, exposed to the test agent, and the second cell, which is not exposed to the test agent; and
   (d) comparing the levels of CSP chaperone activity measured in step (c) in the presence and absence of the test agent, wherein increased levels of CSP chaperone activity in the presence of the test agent relative to the level of CSP chaperone activity in the absence of the test agent indicates that the second agent may be useful for the treatment of Alzheimer's disease.

3. A method for identifying candidate compounds for retarding the onset of Alzheimer's Disease, comprising:
   (a) providing a first cell and a second cell expressing APP, CSP, SGT, and Hsc70;
   (b) contacting the first cell with a test agent;
   (c) measuring the levels of CSP chaperone activity in the first cell, exposed to the test agent, and the second cell, which is not exposed to the test agent; and
   (d) comparing the levels of CSP chaperone activity measured in step (c) in the presence and absence of the test agent, wherein increased levels of CSP chaperone activity in the presence of the test agent relative to the level of CSP chaperone activity in the absence of the test agent indicates that the second agent may be useful for retarding the onset of Alzheimer's disease.

* * * * *